(12) United States Patent
Cheng et al.

(10) Patent No.: US 10,138,273 B2
(45) Date of Patent: Nov. 27, 2018

(54) PEPTIDE LIGANDS FOR HEPATIC STELLATE CELLS

(71) Applicants: Kun Cheng, Kansas City, MO (US); Zhijin Chen, Kansas City, MO (US)

(72) Inventors: Kun Cheng, Kansas City, MO (US); Zhijin Chen, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/288,837

(22) Filed: Oct. 7, 2016

(65) Prior Publication Data

US 2017/0101442 A1     Apr. 13, 2017

Related U.S. Application Data

(60) Provisional application No. 62/238,547, filed on Oct. 7, 2015.

(51) Int. Cl.
| | |
|---|---|
| *A61K 38/04* | (2006.01) |
| *C07K 7/08* | (2006.01) |
| *A61K 47/64* | (2017.01) |
| *A61K 38/00* | (2006.01) |

(52) U.S. Cl.
CPC .............. *C07K 7/08* (2013.01); *A61K 47/64* (2017.08); *A61K 38/00* (2013.01)

(58) Field of Classification Search
None
See application file for complete search history.

(56) References Cited

U.S. PATENT DOCUMENTS

| | | | | |
|---|---|---|---|---|
| 2005/0137329 A1* | 6/2005 | Holmes | ................ | C07K 14/001 525/54.1 |
| 2007/0218001 A1* | 9/2007 | Delagrave | .............. | C07K 14/47 424/9.1 |

FOREIGN PATENT DOCUMENTS

| | | | |
|---|---|---|---|
| CN | 104829693 A | * | 8/2015 |
| DE | 102015003503 A1 | * | 9/2016 |

OTHER PUBLICATIONS

GENESEQ™ Accession No. BCM21838, accessed Aug. 9, 2017.*
GENESEQ™ Accession No. BDE94944, accessed Aug. 9, 2017.*
GENESEQ™ Accession No. BDH78820, accessed Aug. 9, 2017.*
GENESEQ™ Accession No. BDN63058, accessed Aug. 9, 2017.*
GENESEQ™ Accession No. BCQ12655, accessed Aug. 9, 2017.*
GENESEQ™ Accession No. BDE94936, accessed Aug. 9, 2017.*
GENESEQ™ Accession No. BCQ12656, accessed Aug. 9, 2017.*
van Oosten (FEMS Microbiology Reviews, fuv029, 39, 2015, 892-916).*

* cited by examiner

*Primary Examiner* — Christine J Saoud
(74) *Attorney, Agent, or Firm* — Shook, Hardy & Bacon L.L.P.

(57) ABSTRACT

Methods and compositions for identifying and using polypeptides that target hepatic stellate cells are described. Embodiments include a targeting composition that may include one or more polypeptides including an amino acid sequence that binds to an insulin-like growth factor 2 receptor. Other embodiments relate to targeting systems that may include a one or more polypeptides including an amino acid sequence that binds to an insulin-like growth factor 2 receptor of hepatic stellate cells. Further embodiments relate to methods for treating health disorders in which the methods include the targeting composition or targeting systems as well as an agent capable of treating the disorder.

13 Claims, 23 Drawing Sheets
(3 of 23 Drawing Sheet(s) Filed in Color)

Specification includes a Sequence Listing.

| SEQ ID NO. | PHAGE NO. | SEQUENCE | FREQ. |
|---|---|---|---|
| SEQ ID NO: 1 | 408 | G F P T R F E A L S S N | 2 |
| SEQ ID NO: 2 | 420 | G L H T S A T N L Y L H | 1 |
| SEQ ID NO: 3 | 422 | H S F K W L D S P R L R | 1 |
| SEQ ID NO: 4 | 423 | S G V Y K V A Y D G Q H | 1 |
| SEQ ID NO: 5 | 425 | K A S G S P S G F W P S | 1 |
| SEQ ID NO: 6 | 431 | V H W D F R Q W W Q P S | 2 |
| SEQ ID NO: 7 | 436 | R R V D K V Q Y D R Q H | 1 |
| SEQ ID NO: 8 | 439 | G L H T S A L S D L H | 1 |
| SEQ ID NO: 9 | 504 | H T S S L W H L F R S T | 2 |
| SEQ ID NO: 10 | 515 | S G V Y K V A Y D W Q H | 16 |

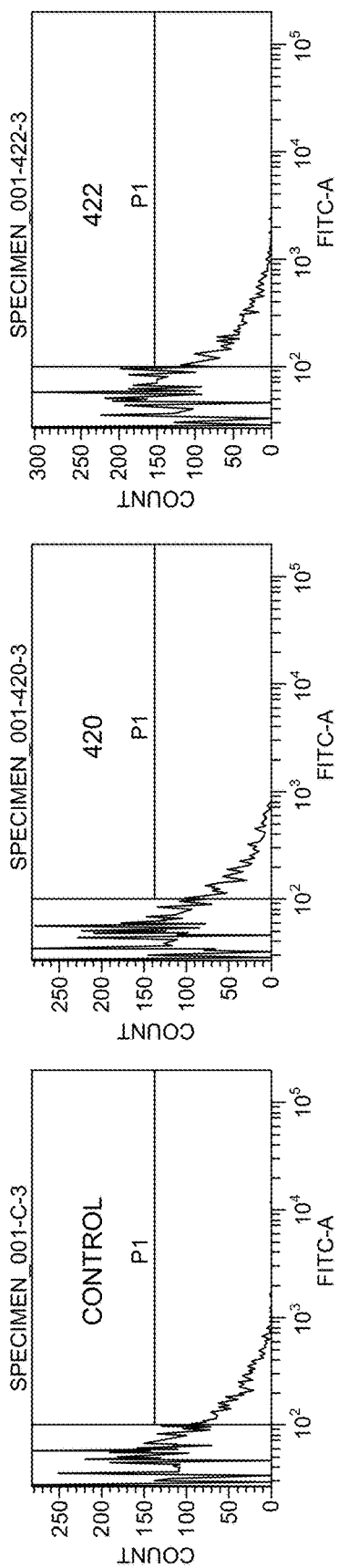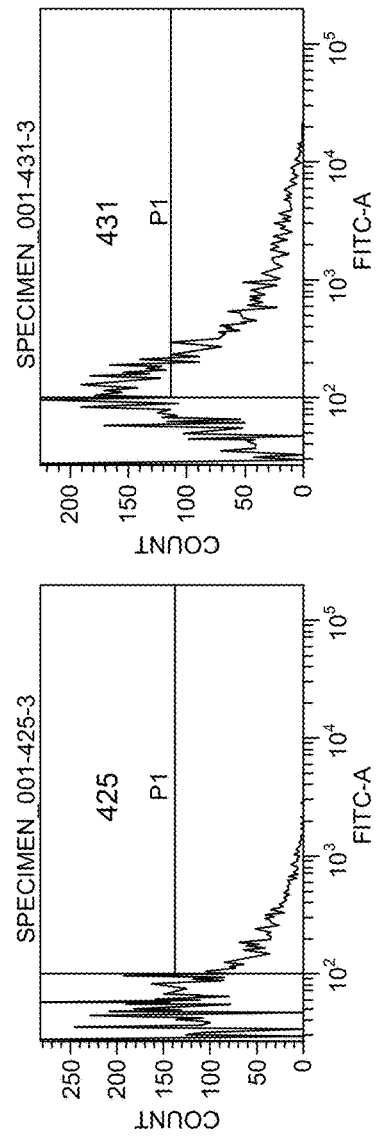
FIG. 8A. FIG. 8B. FIG. 8C. FIG. 8D. FIG. 8E.

| PEPTIDES | 422 | 425 | 431 | 515 |
|---|---|---|---|---|
| $K_d$ ($\mu$M) WITH LX-2 CELLS | 26.52 ± 3.75 | 62.91 ± 6.21 | 6.19 ± 1.90 | 65.00 ± 3.85 |
| $K_d$ ($\mu$M) WITH HSC-T6 CELLS | 402.30 ± 96.50 | N/A | 12.35 ± 0.99 | 57.60 ± 7.91 |

SEQUENCE LISTING

```
<160> NUMBER OF SEQ ID NOS: 14

<210> SEQ ID NO 1
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 1

Gly Phe Pro Thr Arg Phe Glu Ala Leu Ser Ser Asn
1               5                   10

<210> SEQ ID NO 2
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 2

Gly Leu His Thr Ser Ala Thr Asn Leu Tyr Leu His
1               5                   10

<210> SEQ ID NO 3
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 3

His Ser Phe Lys Trp Leu Asp Ser Pro Arg Leu Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 4

Ser Gly Val Tyr Lys Val Ala Tyr Asp Gly Gln His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB
```

```
<400> SEQUENCE: 5

Lys Ala Ser Gly Ser Pro Ser Gly Phe Trp Pro Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 6

Val His Trp Asp Phe Arg Gln Trp Trp Gln Pro Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 7

Arg Arg Val Asp Lys Val Gln Tyr Asp Arg Gln His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 8

Gly Leu His Thr Ser Ala Leu Ser Asp Leu His
1               5                   10

<210> SEQ ID NO 9
<211> LENGTH: 12
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 9

His Thr Ser Ser Leu Trp His Leu Phe Arg Ser Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: M13 Phage Display Peptide Library (Ph.D.-12)
      NEB

<400> SEQUENCE: 10

Ser Gly Tyr Lys Val Ala Tyr Asp Trp Gln His
1               5                   10

<210> SEQ ID NO 11
<211> LENGTH: 2491
```

<212> TYPE: PRT
<213> ORGANISM: Homo sapiens

<400> SEQUENCE: 11

Met Gly Ala Ala Ala Gly Arg Ser Pro His Leu Gly Pro Ala Pro Ala
1               5                   10                  15

Arg Arg Pro Gln Arg Ser Leu Leu Leu Gln Leu Leu Leu Leu Leu Val
            20                  25                  30

Ala Ala Pro Gly Ser Thr Gln Ala Gln Ala Ala Pro Phe Pro Glu Leu
        35                  40                  45

Cys Ser Tyr Thr Trp Glu Ala Val Asp Thr Lys Asn Asn Val Leu Tyr
    50                  55                  60

Lys Ile Asn Ile Cys Gly Ser Val Asp Ile Val Gln Cys Gly Pro Ser
65                  70                  75                  80

Ser Ala Val Cys Met His Asp Leu Lys Thr Arg Thr Tyr His Ser Val
                85                  90                  95

Gly Asp Ser Val Leu Arg Ser Ala Thr Arg Ser Leu Leu Glu Phe Asn
            100                 105                 110

Thr Thr Val Ser Cys Asp Gln Gln Gly Thr Asn His Arg Val Gln Ser
        115                 120                 125

Ser Ile Ala Phe Leu Cys Gly Lys Thr Leu Gly Thr Pro Glu Phe Val
    130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
                165                 170                 175

Phe Asp Glu Glu Leu Arg Lys His Asp Leu Asn Pro Leu Ile Lys Leu
            180                 185                 190

Ser Gly Ala Tyr Leu Val Asp Asp Ser Asp Pro Asp Thr Ser Leu Phe
        195                 200                 205

Ile Asn Val Cys Arg Asp Ile Asp Thr Leu Arg Asp Pro Gly Ser Gln
    210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Glu Ala Gly Lys Leu
            260                 265                 270

Asp Phe Cys Asp Gly His Ser Pro Ala Val Thr Ile Thr Phe Val Cys
        275                 280                 285

Pro Ser Glu Arg Arg Glu Gly Thr Ile Pro Lys Leu Thr Ala Lys Ser
290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
        355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

```
Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
        435                 440                 445

Thr Gly Glu Val Asp Cys Thr Tyr Phe Phe Thr Trp Asp Thr Glu Tyr
    450                 455                 460

Ala Cys Val Lys Glu Lys Glu Asp Leu Leu Cys Gly Ala Thr Asp Gly
465                 470                 475                 480

Lys Lys Arg Tyr Asp Leu Ser Ala Leu Val Arg His Ala Glu Pro Glu
                485                 490                 495

Gln Asn Trp Glu Ala Val Asp Gly Ser Gln Thr Glu Thr Glu Lys Lys
            500                 505                 510

His Phe Phe Ile Asn Ile Cys His Arg Val Leu Gln Glu Gly Lys Ala
        515                 520                 525

Arg Gly Cys Pro Glu Asp Ala Ala Val Cys Ala Val Asp Lys Asn Gly
    530                 535                 540

Ser Lys Asn Leu Gly Lys Phe Ile Ser Ser Pro Met Lys Glu Lys Gly
545                 550                 555                 560

Asn Ile Gln Leu Ser Tyr Ser Asp Gly Asp Cys Gly His Gly Lys
                565                 570                 575

Lys Ile Lys Thr Asn Ile Thr Leu Val Cys Lys Pro Gly Asp Leu Glu
            580                 585                 590

Ser Ala Pro Val Leu Arg Thr Ser Gly Glu Gly Gly Cys Phe Tyr Glu
        595                 600                 605

Phe Glu Trp His Thr Ala Ala Ala Cys Val Leu Ser Lys Thr Glu Gly
    610                 615                 620

Glu Asn Cys Thr Val Phe Asp Ser Gln Ala Gly Phe Ser Phe Asp Leu
625                 630                 635                 640

Ser Pro Leu Thr Lys Lys Asn Gly Ala Tyr Lys Val Glu Thr Lys Lys
                645                 650                 655

Tyr Asp Phe Tyr Ile Asn Val Cys Gly Pro Val Ser Val Ser Pro Cys
            660                 665                 670

Gln Pro Asp Ser Gly Ala Cys Gln Val Ala Lys Ser Asp Glu Lys Thr
        675                 680                 685

Trp Asn Leu Gly Leu Ser Asn Ala Lys Leu Ser Tyr Tyr Asp Gly Met
    690                 695                 700

Ile Gln Leu Asn Tyr Arg Gly Gly Thr Pro Tyr Asn Asn Glu Arg His
705                 710                 715                 720

Thr Pro Arg Ala Thr Leu Ile Thr Phe Leu Cys Asp Arg Asp Ala Gly
                725                 730                 735

Val Gly Phe Pro Glu Tyr Gln Glu Asp Asn Ser Thr Tyr Asn Phe
            740                 745                 750

Arg Trp Tyr Thr Ser Tyr Ala Cys Pro Glu Glu Pro Leu Glu Cys Val
    755                 760                 765

Val Thr Asp Pro Ser Thr Leu Glu Gln Tyr Asp Leu Ser Ser Leu Ala
770                 775                 780

Lys Ser Glu Gly Gly Leu Gly Gly Asn Trp Tyr Ala Met Asp Asn Ser
785                 790                 795                 800

Gly Glu His Val Thr Trp Arg Lys Tyr Tyr Ile Asn Val Cys Arg Pro
                805                 810                 815
```

-continued

Leu Asn Pro Val Pro Gly Cys Asn Arg Tyr Ala Ser Ala Cys Gln Met
            820                 825                 830

Lys Tyr Glu Lys Asp Gln Gly Ser Phe Thr Glu Val Val Ser Ile Ser
        835                 840                 845

Asn Leu Gly Met Ala Lys Thr Gly Pro Val Val Glu Asp Ser Gly Ser
    850                 855                 860

Leu Leu Leu Glu Tyr Val Asn Gly Ser Ala Cys Thr Thr Ser Asp Gly
865                 870                 875                 880

Arg Gln Thr Thr Tyr Thr Thr Arg Ile His Leu Val Cys Ser Arg Gly
                885                 890                 895

Arg Leu Asn Ser His Pro Ile Phe Ser Leu Asn Trp Glu Cys Val Val
            900                 905                 910

Ser Phe Leu Trp Asn Thr Glu Ala Ala Cys Pro Ile Gln Thr Thr Thr
        915                 920                 925

Asp Thr Asp Gln Ala Cys Ser Ile Arg Asp Pro Asn Ser Gly Phe Val
    930                 935                 940

Phe Asn Leu Asn Pro Leu Asn Ser Ser Gln Gly Tyr Asn Val Ser Gly
945                 950                 955                 960

Ile Gly Lys Ile Phe Met Phe Asn Val Cys Gly Thr Met Pro Val Cys
                965                 970                 975

Gly Thr Ile Leu Gly Lys Pro Ala Ser Gly Cys Glu Ala Glu Thr Gln
            980                 985                 990

Thr Glu Glu Leu Lys Asn Trp Lys Pro Ala Arg Pro Val Gly Ile Glu
        995                 1000                1005

Lys Ser Leu Gln Leu Ser Thr Glu Gly Phe Ile Thr Leu Thr Tyr
    1010                1015                1020

Lys Gly Pro Leu Ser Ala Lys Gly Thr Ala Asp Ala Phe Ile Val
    1025                1030                1035

Arg Phe Val Cys Asn Asp Asp Val Tyr Ser Gly Pro Leu Lys Phe
    1040                1045                1050

Leu His Gln Asp Ile Asp Ser Gly Gln Gly Ile Arg Asn Thr Tyr
    1055                1060                1065

Phe Glu Phe Glu Thr Ala Leu Ala Cys Val Pro Ser Pro Val Asp
    1070                1075                1080

Cys Gln Val Thr Asp Leu Ala Gly Asn Glu Tyr Asp Leu Thr Gly
    1085                1090                1095

Leu Ser Thr Val Arg Lys Pro Trp Thr Ala Val Asp Thr Ser Val
    1100                1105                1110

Asp Gly Arg Lys Arg Thr Phe Tyr Leu Ser Val Cys Asn Pro Leu
    1115                1120                1125

Pro Tyr Ile Pro Gly Cys Gln Gly Ser Ala Val Gly Ser Cys Leu
    1130                1135                1140

Val Ser Glu Gly Asn Ser Trp Asn Leu Gly Val Val Gln Met Ser
    1145                1150                1155

Pro Gln Ala Ala Ala Asn Gly Ser Leu Ser Ile Met Tyr Val Asn
    1160                1165                1170

Gly Asp Lys Cys Gly Asn Gln Arg Phe Ser Thr Arg Ile Thr Phe
    1175                1180                1185

Glu Cys Ala Gln Ile Ser Gly Ser Pro Ala Phe Gln Leu Gln Asp
    1190                1195                1200

Gly Cys Glu Tyr Val Phe Ile Trp Arg Thr Val Glu Ala Cys Pro
    1205                1210                1215

Val Val Arg Val Glu Gly Asp Asn Cys Glu Val Lys Asp Pro Arg

```
                1220                1225                1230
His Gly Asn Leu Tyr Asp Leu Lys Pro Leu Gly Leu Asn Asp Thr
    1235                1240                1245
Ile Val Ser Ala Gly Glu Tyr Thr Tyr Phe Arg Val Cys Gly
    1250                1255                1260
Lys Leu Ser Ser Asp Val Cys Pro Thr Ser Asp Lys Ser Lys Val
    1265                1270                1275
Val Ser Ser Cys Gln Glu Lys Arg Glu Pro Gln Gly Phe His Lys
    1280                1285                1290
Val Ala Gly Leu Leu Thr Gln Lys Leu Thr Tyr Glu Asn Gly Leu
    1295                1300                1305
Leu Lys Met Asn Phe Thr Gly Gly Asp Thr Cys His Lys Val Tyr
    1310                1315                1320
Gln Arg Ser Thr Ala Ile Phe Phe Tyr Cys Asp Arg Gly Thr Gln
    1325                1330                1335
Arg Pro Val Phe Leu Lys Glu Thr Ser Asp Cys Ser Tyr Leu Phe
    1340                1345                1350
Glu Trp Arg Thr Gln Tyr Ala Cys Pro Pro Phe Asp Leu Thr Glu
    1355                1360                1365
Cys Ser Phe Lys Asp Gly Ala Gly Asn Ser Phe Asp Leu Ser Ser
    1370                1375                1380
Leu Ser Arg Tyr Ser Asp Asn Trp Glu Ala Ile Thr Gly Thr Gly
    1385                1390                1395
Asp Pro Glu His Tyr Leu Ile Asn Val Cys Lys Ser Leu Ala Pro
    1400                1405                1410
Gln Ala Gly Thr Glu Pro Cys Pro Pro Glu Ala Ala Ala Cys Leu
    1415                1420                1425
Leu Gly Gly Ser Lys Pro Val Asn Leu Gly Arg Val Arg Asp Gly
    1430                1435                1440
Pro Gln Trp Arg Asp Gly Ile Ile Val Leu Lys Tyr Val Asp Gly
    1445                1450                1455
Asp Leu Cys Pro Asp Gly Ile Arg Lys Lys Ser Thr Thr Ile Arg
    1460                1465                1470
Phe Thr Cys Ser Glu Ser Gln Val Asn Ser Arg Pro Met Phe Ile
    1475                1480                1485
Ser Ala Val Glu Asp Cys Glu Tyr Thr Phe Ala Trp Pro Thr Ala
    1490                1495                1500
Thr Ala Cys Pro Met Lys Ser Asn Glu His Asp Asp Cys Gln Val
    1505                1510                1515
Thr Asn Pro Ser Thr Gly His Leu Phe Asp Leu Ser Ser Leu Ser
    1520                1525                1530
Gly Arg Ala Gly Phe Thr Ala Ala Tyr Ser Glu Lys Gly Leu Val
    1535                1540                1545
Tyr Met Ser Ile Cys Gly Glu Asn Glu Asn Cys Pro Pro Gly Val
    1550                1555                1560
Gly Ala Cys Phe Gly Gln Thr Arg Ile Ser Val Gly Lys Ala Asn
    1565                1570                1575
Lys Arg Leu Arg Tyr Val Asp Gln Val Leu Gln Leu Val Tyr Lys
    1580                1585                1590
Asp Gly Ser Pro Cys Pro Ser Lys Ser Gly Leu Ser Tyr Lys Ser
    1595                1600                1605
Val Ile Ser Phe Val Cys Arg Pro Glu Ala Gly Pro Thr Asn Arg
    1610                1615                1620
```

```
Pro Met Leu Ile Ser Leu Asp Lys Gln Thr Cys Thr Leu Phe Phe
    1625            1630            1635

Ser Trp His Thr Pro Leu Ala Cys Glu Gln Ala Thr Glu Cys Ser
    1640            1645            1650

Val Arg Asn Gly Ser Ser Ile Val Asp Leu Ser Pro Leu Ile His
    1655            1660            1665

Arg Thr Gly Gly Tyr Glu Ala Tyr Asp Glu Ser Glu Asp Asp Ala
    1670            1675            1680

Ser Asp Thr Asn Pro Asp Phe Tyr Ile Asn Ile Cys Gln Pro Leu
    1685            1690            1695

Asn Pro Met His Gly Val Pro Cys Pro Ala Gly Ala Ala Val Cys
    1700            1705            1710

Lys Val Pro Ile Asp Gly Pro Pro Ile Asp Ile Gly Arg Val Ala
    1715            1720            1725

Gly Pro Pro Ile Leu Asn Pro Ile Ala Asn Glu Ile Tyr Leu Asn
    1730            1735            1740

Phe Glu Ser Ser Thr Pro Cys Leu Ala Asp Lys His Phe Asn Tyr
    1745            1750            1755

Thr Ser Leu Ile Ala Phe His Cys Lys Arg Gly Val Ser Met Gly
    1760            1765            1770

Thr Pro Lys Leu Leu Arg Thr Ser Glu Cys Asp Phe Val Phe Glu
    1775            1780            1785

Trp Glu Thr Pro Val Val Cys Pro Asp Glu Val Arg Met Asp Gly
    1790            1795            1800

Cys Thr Leu Thr Asp Glu Gln Leu Leu Tyr Ser Phe Asn Leu Ser
    1805            1810            1815

Ser Leu Ser Thr Ser Thr Phe Lys Val Thr Arg Asp Ser Arg Thr
    1820            1825            1830

Tyr Ser Val Gly Val Cys Thr Phe Ala Val Gly Pro Glu Gln Gly
    1835            1840            1845

Gly Cys Lys Asp Gly Gly Val Cys Leu Leu Ser Gly Thr Lys Gly
    1850            1855            1860

Ala Ser Phe Gly Arg Leu Gln Ser Met Lys Leu Asp Tyr Arg His
    1865            1870            1875

Gln Asp Glu Ala Val Val Leu Ser Tyr Val Asn Gly Asp Arg Cys
    1880            1885            1890

Pro Pro Glu Thr Asp Asp Gly Val Pro Cys Val Phe Pro Phe Ile
    1895            1900            1905

Phe Asn Gly Lys Ser Tyr Glu Glu Cys Ile Ile Glu Ser Arg Ala
    1910            1915            1920

Lys Leu Trp Cys Ser Thr Thr Ala Asp Tyr Asp Arg Asp His Glu
    1925            1930            1935

Trp Gly Phe Cys Arg His Ser Asn Ser Tyr Arg Thr Ser Ser Ile
    1940            1945            1950

Ile Phe Lys Cys Asp Glu Asp Glu Asp Ile Gly Arg Pro Gln Val
    1955            1960            1965

Phe Ser Glu Val Arg Gly Cys Asp Val Thr Phe Glu Trp Lys Thr
    1970            1975            1980

Lys Val Val Cys Pro Pro Lys Lys Leu Glu Cys Lys Phe Val Gln
    1985            1990            1995

Lys His Lys Thr Tyr Asp Leu Arg Leu Leu Ser Ser Leu Thr Gly
    2000            2005            2010
```

```
Ser Trp Ser Leu Val His Asn Gly Val Ser Tyr Tyr Ile Asn Leu
2015                2020                2025

Cys Gln Lys Ile Tyr Lys Gly Pro Leu Gly Cys Ser Glu Arg Ala
2030                2035                2040

Ser Ile Cys Arg Arg Thr Thr Gly Asp Val Gln Val Leu Gly
2045                2050                2055

Leu Val His Thr Gln Lys Leu Gly Val Ile Gly Asp Lys Val Val
2060                2065                2070

Val Thr Tyr Ser Lys Gly Tyr Pro Cys Gly Gly Asn Lys Thr Ala
2075                2080                2085

Ser Ser Val Ile Glu Leu Thr Cys Thr Lys Thr Val Gly Arg Pro
2090                2095                2100

Ala Phe Lys Arg Phe Asp Ile Asp Ser Cys Thr Tyr Tyr Phe Ser
2105                2110                2115

Trp Asp Ser Arg Ala Ala Cys Ala Val Lys Pro Gln Glu Val Gln
2120                2125                2130

Met Val Asn Gly Thr Ile Thr Asn Pro Ile Asn Gly Lys Ser Phe
2135                2140                2145

Ser Leu Gly Asp Ile Tyr Phe Lys Leu Phe Arg Ala Ser Gly Asp
2150                2155                2160

Met Arg Thr Asn Gly Asp Asn Tyr Leu Tyr Glu Ile Gln Leu Ser
2165                2170                2175

Ser Ile Thr Ser Ser Arg Asn Pro Ala Cys Ser Gly Ala Asn Ile
2180                2185                2190

Cys Gln Val Lys Pro Asn Asp Gln His Phe Ser Arg Lys Val Gly
2195                2200                2205

Thr Ser Asp Lys Thr Lys Tyr Tyr Leu Gln Asp Gly Asp Leu Asp
2210                2215                2220

Val Val Phe Ala Ser Ser Ser Lys Cys Gly Lys Asp Lys Thr Lys
2225                2230                2235

Ser Val Ser Ser Thr Ile Phe Phe His Cys Asp Pro Leu Val Glu
2240                2245                2250

Asp Gly Ile Pro Glu Phe Ser His Glu Thr Ala Asp Cys Gln Tyr
2255                2260                2265

Leu Phe Ser Trp Tyr Thr Ser Ala Val Cys Pro Leu Gly Val Gly
2270                2275                2280

Phe Asp Ser Glu Asn Pro Gly Asp Asp Gly Gln Met His Lys Gly
2285                2290                2295

Leu Ser Glu Arg Ser Gln Ala Val Gly Ala Val Leu Ser Leu Leu
2300                2305                2310

Leu Val Ala Leu Thr Cys Cys Leu Leu Ala Leu Leu Leu Tyr Lys
2315                2320                2325

Lys Glu Arg Arg Glu Thr Val Ile Ser Lys Leu Thr Thr Cys Cys
2330                2335                2340

Arg Arg Ser Ser Asn Val Ser Tyr Lys Tyr Ser Lys Val Asn Lys
2345                2350                2355

Glu Glu Glu Thr Asp Glu Asn Glu Thr Glu Trp Leu Met Glu Glu
2360                2365                2370

Ile Gln Leu Pro Pro Pro Arg Gln Gly Lys Glu Gly Gln Glu Asn
2375                2380                2385

Gly His Ile Thr Thr Lys Ser Val Lys Ala Leu Ser Ser Leu His
2390                2395                2400

Gly Asp Asp Gln Asp Ser Glu Asp Glu Val Leu Thr Ile Pro Glu
```

```
              2405                2410                2415
Val Lys Val His Ser Gly Arg Gly Ala Gly Ala Glu Ser Ser His
    2420                2425                2430

Pro Val Arg Asn Ala Gln Ser Asn Ala Leu Gln Glu Arg Glu Asp
    2435                2440                2445

Asp Arg Val Gly Leu Val Arg Gly Glu Lys Ala Arg Lys Gly Lys
    2450                2455                2460

Ser Ser Ser Ala Gln Gln Lys Thr Val Ser Ser Thr Lys Leu Val
    2465                2470                2475

Ser Phe His Asp Asp Ser Asp Glu Asp Leu Leu His Ile
    2480                2485                2490

<210> SEQ ID NO 12
<211> LENGTH: 1926
<212> TYPE: PRT
<213> ORGANISM: Rattus rattus

<400> SEQUENCE: 12

Met Arg Ala Val Leu Pro Gly Pro Val Pro Ser Gly Pro Arg Val Ala
1               5                   10                  15

Leu Leu Leu Pro Leu Leu Leu Leu Leu Val Ala Ala Ala Gly Ser
                20                  25                  30

Ala Gln Ala Gln Ala Val Asp Leu Asp Ala Leu Cys Ser Tyr Thr Trp
            35                  40                  45

Glu Ala Val Asp Ser Lys Asn Asn Ala Val Tyr Lys Ile Asn Pro Cys
        50                  55                  60

Gly His Val Asp Asn Pro Arg Cys Gly Pro Thr Ser Ala Val Cys Met
65                  70                  75                  80

Cys Asp Leu Lys Ser Glu Asn Cys Arg Ser Val Gly Asp Ser Leu Leu
                85                  90                  95

Arg Ser Ser Ala Lys Ser Leu Leu Glu Phe Asn Thr Thr Thr Gly Cys
                100                 105                 110

Gln Pro Ser Glu His Arg Ile Gln Thr Ser Ile Thr Phe Leu Cys Gly
            115                 120                 125

Lys Thr Leu Gly Thr Pro Glu Phe Val Thr Ala Thr Asp Cys Val His
130                 135                 140

Tyr Phe Glu Trp Arg Thr Thr Ala Ala Cys Lys Lys Asp Ile Phe Lys
145                 150                 155                 160

Ala Asp Lys Glu Val Pro Cys Tyr Val Phe Asp Asp Lys Leu Gln Lys
                165                 170                 175

His Asp Leu Asn Pro Leu Ile Lys Leu Asn Gly Gly Tyr Leu Val Asp
            180                 185                 190

Asp Ser Asp Ala Asp Ala Ser Leu Phe Ile Asn Val Cys Arg Asp Ile
        195                 200                 205

Asp Ser Leu Arg Asp Pro Ser Thr Gln Leu Arg Val Cys Pro Ala Gly
    210                 215                 220

Thr Ala Ala Cys Leu Leu Lys Gly Asn Gln Ala Phe Asp Val Gly Arg
225                 230                 235                 240

Pro Lys Glu Gly Leu Lys Leu Leu Ser Lys Asp Arg Leu Val Leu Thr
                245                 250                 255

Tyr Val Lys Glu Glu Gly Glu Lys Pro Asp Phe Cys Asn Gly His Ser
            260                 265                 270

Pro Ala Val Thr Val Thr Phe Val Cys Pro Ser Glu Arg Arg Glu Gly
        275                 280                 285
```

-continued

Thr Ile Pro Lys Leu Thr Ala Lys Ser Asn Cys Arg Tyr Glu Val Glu
290                 295                 300

Trp Ile Thr Glu Tyr Ala Cys His Arg Asp Tyr Leu Glu Ser Glu Thr
305                 310                 315                 320

Cys Ser Leu Ser Ser Glu Gln His Asp Ile Ala Ile Asp Leu Ser Pro
            325                 330                 335

Leu Ala Gln His Glu Glu Gly Ser Pro Tyr Val Ala Asp Gly Gly Glu
            340                 345                 350

Tyr Arg Phe Phe Met Asn Val Cys Gly Asp Thr Lys Val Ser Leu Cys
            355                 360                 365

Asn Lys Glu Ala Ala Val Cys Gln Glu Lys Lys Val Asp Ser Thr Gln
370                 375                 380

Val Lys Ile Ala Gly Arg His Gln Asn Gln Thr Leu Arg Tyr Ser Asp
385                 390                 395                 400

Gly Asp Leu Thr Leu Ile Tyr Ser Gly Gly Asp Glu Cys Ser Ser Gly
                405                 410                 415

Phe Gln Arg Met Ser Val Ile Asn Phe Glu Cys Asn Lys Thr Ala Gly
            420                 425                 430

Gln Asp Gly Arg Gly Glu Pro Val Phe Thr Gly Glu Val Asp Cys Thr
            435                 440                 445

Tyr Phe Phe Thr Trp Asp Thr Lys Tyr Ala Cys Val Lys Glu Lys Glu
450                 455                 460

Asp Leu Leu Cys Gly Ala Ile Asp Gly Lys Lys Arg Tyr Asp Leu Ser
465                 470                 475                 480

Val Leu Ala Arg His Ser Glu Ser Glu Gln Asn Trp Glu Ala Val Asp
                485                 490                 495

Gly Ser Gln Ala Glu Ser Glu Lys Arg Asn Phe Phe Ile Asn Val Cys
            500                 505                 510

His Arg Val Leu Gln Ala Gly Lys Ala Lys Asn Cys Pro Glu Gly Ala
            515                 520                 525

Ala Val Cys Ala Val Asp Lys Ser Gly Ser Lys Asn Leu Gly Lys Phe
530                 535                 540

Val Ser Ser Pro Thr Lys Glu Lys Gly His Ile Gln Leu Ser Tyr Ser
545                 550                 555                 560

Asp Gly Asp Asp Cys Gly Asn Asp Lys Lys Ile Thr Thr Asn Ile Thr
                565                 570                 575

Phe Val Cys Lys Pro Gly Asp Leu Glu Ser Ala Pro Val Leu Arg Ala
            580                 585                 590

Ala Gly Pro Asp Gly Cys Ser Tyr Glu Phe Glu Trp His Thr Ala Ala
            595                 600                 605

Ala Cys Val Leu Ser Gln Thr Glu Gly Glu Asn Cys Thr Val Leu Asp
610                 615                 620

Ala Gln Ala Gly Phe Ser Phe Asp Leu Ser Leu Leu Thr Lys Lys Asn
625                 630                 635                 640

Gly Ala Tyr Lys Val Glu Thr Asp Lys Tyr Asp Phe Tyr Ile Asn Val
                645                 650                 655

Cys Gly Pro Val Ser Val Asn Leu Cys Gln Ser Asn Ser Gly Ala Cys
            660                 665                 670

Gln Val Ala Lys Ser Gly Lys Ser Trp Asn Leu Gly Leu Ser Asn Thr
            675                 680                 685

Lys Leu Thr Tyr Tyr Asp Gly Met Ile Gln Leu Ser Tyr Arg Asn Gly
690                 695                 700

Thr Leu Tyr Asn Asn Glu Lys His Thr Pro Arg Ser Thr Leu Ile Thr

-continued

```
            705                 710                 715                 720
        Phe Leu Cys Asp Arg Asp Ala Gly Val Gly Phe Pro Glu Tyr Gln Glu
                        725                 730                 735
        Glu Asp Asn Ser Thr Tyr Asn Phe Arg Trp Tyr Thr Ser Tyr Ala Cys
                        740                 745                 750
        Pro Glu Glu Pro Leu Glu Cys Met Val Thr Asp Pro Ser Met Met Glu
                        755                 760                 765
        Gln Tyr Asp Leu Ser Ser Leu Val Lys Phe Gly Gly Arg Gly Gly
                        770                 775                 780
        Asn Trp Tyr Ala Met Glu Asn Ser Arg Glu His Phe Thr Arg Arg Lys
        785                 790                 795                 800
        Tyr Tyr Leu Asn Val Cys Arg Pro Leu Asn Pro Val Pro Gly Cys Asp
                        805                 810                 815
        Arg Tyr Ala Ser Ala Cys Gln Met Lys Tyr Glu Asn Asn Glu Gly Ser
                        820                 825                 830
        Leu Ala Glu Thr Val Ala Ile Ser Asn Leu Gly Val Ala Lys Thr Gly
                        835                 840                 845
        Pro Val Val Glu Glu Ser Gly Ser Leu Leu Leu Glu Tyr Val Asn Gly
                        850                 855                 860
        Ser Ala Cys Thr Thr Ser Asp Gly Arg Leu Thr Thr Tyr Ser Thr Arg
        865                 870                 875                 880
        Ile His Leu Val Cys Gly Arg Gly Thr Met Asn Ser His Pro Ile Phe
                        885                 890                 895
        Thr Phe Asn Trp Glu Cys Val Val Ser Phe Leu Trp Asn Thr Glu Ala
                        900                 905                 910
        Ala Cys Pro Ile Gln Thr Ile Thr Asp Ser Asp Gln Ala Cys Ser Ile
                        915                 920                 925
        Arg Asp Pro Asn Ser Gly Phe Val Phe Asn Leu Ser Pro Leu Asn Tyr
                        930                 935                 940
        Ser Gln Gly His Met Val Leu Gly Ile Gly Lys Thr Phe Val Phe Asn
        945                 950                 955                 960
        Ile Cys Gly Thr Met Pro Ala Cys Gly Thr Val Ala Gly Lys Pro Ala
                        965                 970                 975
        Leu Gly Cys Glu Ala Glu Thr Lys Ile Lys Asp Ile Lys Asp Leu Lys
                        980                 985                 990
        Pro Glu Arg Pro Val Gly Met Glu Lys Ser Leu Gln Leu Ser Ala Glu
                        995                 1000                1005
        Gly Phe Leu Thr Leu Thr Tyr Lys Gly Ser Ser Pro Ser Asp Arg
                        1010                1015                1020
        Gly Thr Ala Phe Ile Ile Arg Phe Ile Cys Asn Gly Asp Ile Tyr
                        1025                1030                1035
        Pro Gly Thr Pro Lys Phe Leu His Gln Asp Ile Asp Ser Ala Arg
                        1040                1045                1050
        Gly Ile Arg Asn Thr Phe Phe Glu Phe Glu Thr Ala Leu Ala Cys
                        1055                1060                1065
        Ile Pro Ser Val Val Asp Cys Gln Val Thr Asp Pro Ala Gly Asn
                        1070                1075                1080
        Glu Tyr Asp Leu Ser Ala Leu Ser Met Val Arg Lys Pro Trp Thr
                        1085                1090                1095
        Ala Val Asp Thr Ser Val His Gly Lys Lys Arg Arg Phe Tyr Leu
                        1100                1105                1110
        Ser Val Cys Thr Pro Leu Pro Tyr Ile Pro Gly Cys Asp Gly Ile
                        1115                1120                1125
```

```
Ala Met Gly Ser Cys Met Val Ser Glu Asp Lys Ser Gln Asn Leu
1130                1135                1140

Gly Val Val Gln Ile Ser Pro Gln Ala Thr Gly Asn Gly Ser Leu
    1145                1150                1155

Ser Ile Leu Tyr Val Asn Gly Asp Arg Cys Gly Asn Gln Arg Tyr
    1160                1165                1170

Ser Thr Arg Ile Val Phe Glu Cys Ala Gln Thr Ser Gly Ser Pro
    1175                1180                1185

Met Phe Gln Leu Leu Asn Asn Cys Glu Tyr Val Phe Val Trp Arg
    1190                1195                1200

Thr Val Glu Ala Cys Pro Val Val Arg Glu Glu Gly Asp Asn Cys
    1205                1210                1215

Gln Val Lys Asp Pro Arg His Gly Asn Leu Tyr Asp Leu Lys Pro
    1220                1225                1230

Leu Ala Leu Asn Asp Thr Ile Ile Ser Ala Gly Glu Tyr Thr Tyr
    1235                1240                1245

Tyr Phe Arg Val Cys Gly Lys Leu Ser Leu Asp Val Cys Ser Ala
    1250                1255                1260

His Asp Gly Ser Lys Ala Val Ser Ser Cys Gln Glu Lys Lys Gly
    1265                1270                1275

Pro Gln Gly Phe Gln Lys Val Ala Gly Leu Leu Asn Gln Lys Leu
    1280                1285                1290

Thr Phe Glu Asn Gly Leu Leu Lys Met Asn Tyr Ser Gly Gly Asp
    1295                1300                1305

Thr Cys His Lys Val Tyr Gln Arg Ser Thr Thr Ile Tyr Phe Tyr
    1310                1315                1320

Cys Asp Arg Thr Thr Gln Lys Pro Val Phe Leu Lys Glu Thr Leu
    1325                1330                1335

Asp Cys Ser Tyr Leu Phe Glu Trp Arg Thr Gln Tyr Ala Cys Pro
    1340                1345                1350

Pro Phe Asn Val Thr Glu Cys Ser Ile Gln Asp Glu Ala Gly Asn
    1355                1360                1365

Ser Ile Asp Leu Ser Ser Leu Ser Arg Tyr Ser Asp Asn Trp Glu
    1370                1375                1380

Ala Val Thr Arg Thr Gly Ala Thr Glu His Tyr Leu Ile Asn Val
    1385                1390                1395

Cys Lys Ser Leu Ser Pro Gln Ala Gly Thr Asp Pro Cys Pro Pro
    1400                1405                1410

Glu Ala Ala Val Cys Leu Leu Asp Gly Ser Lys Pro Val Asn Leu
    1415                1420                1425

Gly Arg Val Arg Asp Gly Pro Gln Trp Thr Ala Gly Val Thr Val
    1430                1435                1440

Leu Lys Tyr Val Asp Gly Asp Leu Cys Pro Asp Lys Ile Arg Lys
    1445                1450                1455

Arg Ser Thr Ile Ile Arg Phe Thr Cys Ser Asp Ser Gln Val Asn
    1460                1465                1470

Ser Arg Pro Leu Phe Ile Ser Ala Val Gln Asp Cys Glu Tyr Thr
    1475                1480                1485

Phe Ser Trp Pro Thr Pro Ala Ala Cys Pro Val Lys Ser Asn Ile
    1490                1495                1500

His Asp Asp Cys Gln Val Thr Asn Pro Ser Thr Gly His Leu Phe
    1505                1510                1515
```

```
Asp Leu Ser Ser Leu Ser Gly Lys Ala Gly Ile Thr Ala Ser Tyr
    1520                1525                1530

Ser Glu Lys Gly Met Val Phe Met Ser Ile Cys Glu Glu Asn Val
1535                1540                    1545

Asn Cys Ser Pro Gly Val Gly Ala Cys Phe Gly Gln Thr Arg Ile
    1550                1555                1560

Ser Val Gly Gln Ala Ser Lys Arg Leu Ser Tyr Lys Asp Gln Val
    1565                1570                1575

Leu Gln Leu Val Tyr Glu Asn Gly Ser Pro Cys Pro Ser Lys Ser
    1580                1585                1590

Gly Leu Arg Tyr Lys Ser Val Ile Ser Phe Val Cys Arg Pro Glu
    1595                1600                1605

Ala Gly Pro Thr Asn Arg Pro Met Leu Ile Ser Leu Asp Lys Gln
    1610                1615                1620

Ser Cys Thr Leu Phe Phe Ser Trp His Thr Pro Leu Ala Cys Glu
    1625                1630                1635

Gln Ala Thr Glu Cys Thr Val Arg Asn Gly Ser Ser Ile Ile Asp
    1640                1645                1650

Leu Ser Pro Leu Ile His Arg Thr Gly Gly Tyr Glu Ala Tyr Asp
    1655                1660                1665

Glu Ser Glu Asp Asp Thr Ser Asp Thr Thr Pro Asp Phe Tyr Ile
    1670                1675                1680

Asn Ile Cys Gln Pro Leu Asn Pro Met His Gly Val Pro Cys Pro
    1685                1690                1695

Ala Gly Ala Ser Val Cys Lys Val Pro Val Asp Gly Pro Pro Ile
    1700                1705                1710

Asp Ile Gly Arg Val Thr Gly Pro Pro Ile Phe Asn Pro Val Ala
    1715                1720                1725

Asn Glu Val Tyr Leu Asn Phe Glu Ser Ser Thr Pro Cys Leu Ala
    1730                1735                1740

Asp Lys Tyr Met Asn Tyr Thr Ser Leu Ile Ala Phe His Cys Arg
    1745                1750                1755

Arg Gly Ile Ser Met Val Thr Arg Asp Ala His Thr Tyr Ser Ile
    1760                1765                1770

Gly Val Cys Thr Thr Ala Ala Asp Leu Asp Gln Glu Gly Cys Lys
    1775                1780                1785

Asp Gly Gly Val Cys Leu Leu Ser Gly Ser Lys Gly Ala Ser Phe
    1790                1795                1800

Gly Arg Leu Ala Ser Met Gln Leu Asp Tyr Arg His Gln Asp Glu
    1805                1810                1815

Ala Val Ile Leu Ser Tyr Val Asn Gly Asp Pro Cys Pro Pro Glu
    1820                1825                1830

Thr Glu Asp Gly Glu Pro Cys Val Phe Pro Phe Ile Tyr Lys Gly
    1835                1840                1845

Glu Thr Tyr Asp Glu Cys Val Leu Glu Gly Arg Ala Lys Leu Trp
    1850                1855                1860

Cys Ser Lys Thr Ala Asn Tyr Asp Arg Asp His Glu Trp Gly Phe
    1865                1870                1875

Cys Arg Pro Ser Thr Leu Ser Ile Cys Ala Lys Glu Tyr Ile Lys
    1880                1885                1890

Val Pro Trp Thr Ala Leu Arg Glu Pro Ala Phe Ala Arg Arg Val
    1895                1900                1905

Pro Leu Val Lys Ser Arg Phe Trp Gly Leu Phe Ile Leu Lys Asn
```

```
               1910            1915            1920
Trp Lys  Ser
     1925

<210> SEQ ID NO 13
<211> LENGTH: 14
<212> TYPE: PRT
<213> ORGANISM: Artificial Sequence
<220> FEATURE:
<223> OTHER INFORMATION: proapoptotic peptide

<400> SEQUENCE: 13

Lys Leu Ala Lys Leu Ala Lys Lys Leu Ala Lys Leu Ala Lys
1               5                   10

<210> SEQ ID NO 14
<211> LENGTH: 20
<212> TYPE: DNA
<213> ORGANISM: Artificial Sequence
<220> FEATURE:
<223> OTHER INFORMATION: Primer for sequencing of Phage Display Library

<400> SEQUENCE: 14
ccctcatagt tagcgtaacg                                          20
```

PEPTIDE LIGANDS FOR HEPATIC STELLATE CELLS

CROSS-REFERENCE TO RELATED APPLICATIONS

This application claims priority to U.S. Provisional Application No. 62/238,547, filed Oct. 7, 2015 and entitled "Peptide Ligands for Hepatic Stellate Cells." The entirety of the aforementioned application is incorporated by reference herein.

GRANT STATEMENT

This invention was made with Government support under Grant No. 1R01AA021510 awarded by the National Institutes of Health. The Government has certain rights in the invention.

FIELD OF THE INVENTION

The present invention relates to methods and chemical compositions for identifying and using peptides that selectively target hepatic stellate cells (hereinafter "HSCs") in mammals.

SEQUENCE LISTING

A text file in compliance with ASCII and having a ".txt" extension has been electronically submitted via EFS-Web. The text file named "Sequence Listing" was created on Oct. 7, 2016 and is 40.4 KB. The text file is expressly incorporated by reference herein in its entirety.

BACKGROUND

Liver fibrosis is a global health problem and one of the leading causes of morbidity and mortality in western developed countries. Liver fibrosis may be caused by chronic liver damage, such as hepatitis, alcohol abuse, and nonalcoholic steatohepatitis. Regardless of its cause, liver fibrosis is characterized by the excessive accumulation of extracellular matrix ("ECM") in the liver. HSCs are the main producers responsible for the excessive production of ECM and pro-fibrogenic cytokines in fibrotic liver. Therefore, development of HSC-specific delivery systems is essential for the success of antifibrotic agents.

The insulin-like growth factor 2 receptor ("IGF2R"), also known as cation-independent mannose-6-phosphate receptor (M6PR), is a member of the IGF signaling system. IGF2R is a 300 kDa glycoprotein containing three domains, the cytoplasmic domain, transmembrane domain, and extracellular domain. The major function of IGF2R is to regulate lysosomal enzymes such as growth factor IGF2 by transporting them into lysosomes, followed by digestion by lysosomal acid hydrolases. IGF2R is expressed in HSCs, and its expression is upregulated during liver fibrogenisis. Moreover, IGF2R can internalize extracellular ligands, and therefore it can be adopted as a target receptor for HSC-specific drug delivery.

Conventional methods for delivering drugs to HSCs have limitations including inefficient uptake. Recently, drug delivery systems have utilized peptides because of their high binding affinity, ease of syntheses, and the ability to identify peptides that target specific proteins, cells, and tissues. Nevertheless, no peptides have been identified to specifically target IGF2R. Therefore, there is a need to identify IGF2R-specific peptides that can be used in various applications which target IGF2R.

BRIEF SUMMARY

Embodiments of the present invention describe methods to identify and generate polypeptides that target IGF2R or IGF2R-specific peptides. Further embodiments describe targeting compositions that can include one or more polypeptides that interact with or bind to IGF2R. In some embodiments, the targeting composition including one or more polypeptides that interact with or bind to IGF2R may be used in applications related to HSCs, such as therapeutic or research applications. Other embodiments describe a targeting composition including one or more polypeptides that may also comprise at least one agent from a group including an anti-fibrotic agent, an anti-cancer agent, a proapoptotic agent, or an imaging agent. In additional embodiments, the targeting compositions may include a polypeptide comprising an amino acid sequence having at least 90% sequence identity to the amino acid sequence of SEQ ID NO: 6, where the polypeptide is configured to bind to at least a portion of an insulin-like growth factor 2 receptor (IGF2R).

In a first aspect, a targeting composition is provided that comprises a polypeptide comprising an amino acid sequence having at least 95% sequence identity to the amino acid sequence of SEQ ID NO: 6, where the polypeptide is configured to bind to at least a portion of an insulin-like growth factor 2 receptor (IGF2R).

In a second aspect, a Hepatic stellate cell (HSC) targeting system is provided that comprises a polypeptide comprising an amino acid sequence having at least 90% sequence identity to the amino acid sequence of SEQ ID NO: 6, where the polypeptide is configured to bind to at least a portion of an insulin-like growth factor 2 receptor (IGF2R) associated with Hepatic stellate cells (HSCs).

In a third aspect, a Hepatic stellate cell (HSC) targeting system is provided that comprises a targeting composition. The targeting composition comprises a dimeric polypeptide, wherein the dimeric polypeptide comprises a first and a second amino acid sequence. Each of the first and second amino acid sequences comprises an amino acid sequence having at least 95% sequence identity to the amino acid sequence of SEQ ID NO: 6, and wherein the first and second amino acid sequences are linked to one another via a linking moiety. The targeting composition further comprises at least one of an anti-fibrotic agent, an anti-cancer agent, a proapoptotic agent, or an imaging agent. At least a portion of the dimeric polypeptide is configured to bind to at least a portion of an insulin-like growth factor 2 receptor (IGF2R) associated with HSCs.

BRIEF DESCRIPTION OF THE DRAWINGS

Embodiments are described in detail below with reference to the attached drawing figures. The patent or application file contains at least one drawing executed in color. Copies of this patent or patent application publication with color drawing(s) will be provided by the Office upon request and payment of the necessary fee.

FIGS. 8A-8G show cellular uptake of identified peptides in LX-2 cells;

DETAILED DESCRIPTION

Figure 1:
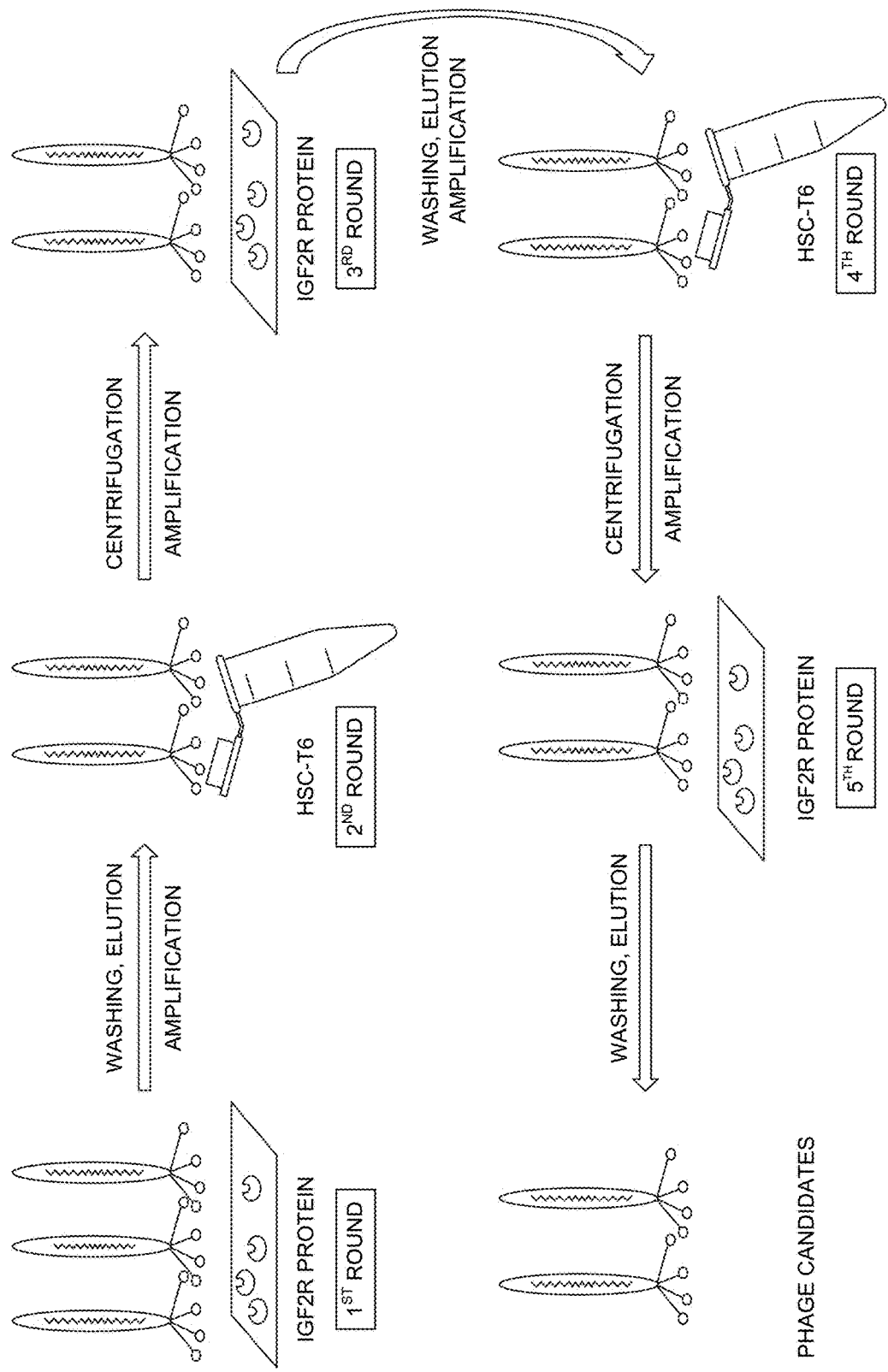
FIG. 1 illustrates a combinatorial phage biopanning procedure conducted to identify polypeptides target IGFR2.

The present invention is directed towards methods and chemical compositions, which involve identifying certain polypeptides and using those polypeptides to aid in diagnosis, prevention, and/or treatment of disorders, e.g., disorders associated with the liver. The identified peptides may also be used in connection with other disorders in which IGF2R is highly expressed.

Throughout this disclosure, the terms "peptide" and "polypeptide" are used interchangeably. Thus, unless specifically noted otherwise, "peptide" and "polypeptide" shall not limit one or the other, but shall be construed to have the same, broadest meaning.

Many of the embodiments of the present invention involve the attachment, bonding, joining, or linking of various compounds. In some instances, the term a "linking moiety" is used to refer to these aspects. As such, "linking moiety" is meant to include any conventional linking moieties known to one skilled in the art that can covalently link two peptide sequences together, such as another amino acid residue, e.g. lysine. The linking moiety may also comprise aminohexanoic acid; $(CH_2)_4$; $(CH_2)_5$; $(CH_2)_6$; $(CH_2)_7$; $(CH_2)_8$ or a combination thereof.

Furthermore, the term "attachment moiety" may be used to describe the connection or joining of an agent to a polypeptide. The term "attachment moiety" shall include any conventional attachment moiety known to one skilled in the art that can covalently link a therapeutic agent to the polypeptide, including amino acid residues, small molecules, peptides, proteins, nucleic acids, polymers, lipids, inorganic nanoparticles, imaging agents, and radioisotopes.

In certain embodiments, an imaging agent is attached or included with a targeting composition or system. An imaging agent shall include any suitable imaging agent known in the art.

Embodiments of the present invention relate to a targeting composition. Generally, the targeting composition comprises a peptide sequence or amino acid sequence and is configured to bind with at least a portion of an IGF2R. In some embodiments, the targeting composition may also comprise a peptide or a polypeptide, which includes a specific peptide or amino acid sequence. In even further embodiments, the targeting composition may also include an agent.

In specific embodiments, the targeting composition comprises a peptide sequence included in a peptide ligand capable of targeting IGF2R. As identified through the methods further describe below, 10 peptide ligands were found to bind with IGF2R. The amino acid sequences of these peptide ligands are identified as SEQ ID NOS: 1-10. The peptide ligand was referred to as Peptide-431 and through methods discussed herein, was determined to include a peptide sequence of "VHWDFRQWWQPS" identified as SEQ ID NO: 6. For purpose of clarity throughout this application, the sequence of Peptide-431, shall be referred to as the amino acid sequence of SEQ ID NO: 6. Thus, in embodiments, the targeting composition comprises the amino acid sequence of SEQ ID NO: 6 or an amino acid sequence with at least 70%, 80%, 90%, 95%, or 99% sequence identity to the amino acid sequence of SEQ ID NO: 6. In embodiments, the amino acid sequence in the targeting compositions can include L-amino acids. In certain embodiments, the amino acid sequence present in the targeting compositions disclosed herein can include D-amino acids.

Other embodiments of the targeting composition may comprise multiple amino acid sequences, which may be held together by a linking compound such as a linking moiety. Said differently, the targeting composition may comprise dimers or trimers that include duplicates or triplicates of an amino acid sequence. Particularly, the targeting composition may comprise a dimer with a first amino acid sequence and a second amino acid sequence, both of which comprise an amino acid sequence having at least 70%, 80%, 90%, 95%, or 99% or 100% sequence identity to the amino acid sequence of SEQ ID NO: 6. To this same extent, a trimer would include three of the amino acid sequences having at least 70%, 80%, 90%, 95%, or 99% or 100% sequence identity to the amino acid sequence of SEQ ID NO: 6.

In further embodiments, the targeting composition comprises a polypeptide that is configured to bind to at least a portion of an IGF2R. In some embodiments the polypeptide may comprise Peptide-431. In other embodiments, the polypeptide comprises an amino acid sequence that has at least 70%, 80%, 90%, 95%, or 99% sequence identity to the amino acid sequence of SEQ ID NO: 6. Moreover, the polypeptide may comprise the amino acid sequence of SEQ ID NO: 6, which in some embodiments, includes D-amino acids or L-amino acids. In additional embodiments, the polypeptide may comprise multiple amino acid sequences, which may be held together by a linking compound such as a linking moiety. In certain aspects, the polypeptide may comprise dimers or trimers that include duplicates or triplicates of amino acid sequences. For example, the polypeptide may comprise a dimer with a first amino acid sequence and a second amino acid sequence, both of which include the amino acid sequence having at least 70%, 80%, 90%, 95%, or 99% or 100% sequence identity to the amino acid sequence of SEQ ID NO: 6.

In additional embodiments, the targeting composition comprises an agent, which may include an anti-fibrotic agent, an anti-cancer agent, a proapoptotic agent, or an imaging agent. The agent may be attached to the targeting composition using conventional means known by those in the art, and thus, in some embodiments the agent is covalently attached to the polypeptide. Additionally, the agents may include any agents known in the art that perform the literal function of the respective agent.

In even more embodiments, the targeting composition is configured to bind with IGF2R. Through various methods and experiments, which are discussed herein, Peptide-431 was identified as having a high bonding affinity and high specificity for IGF2R. As mentioned, Peptide-431's targeting of IGF2R is due to the amino acid sequence of SEQ ID NO: 6. In certain embodiments, the targeting composition may consist solely of the amino acid sequence of SEQ ID NO: 6 or may comprise a polypeptide that fractionally include the amino acid sequence of SEQ ID NO: 6. In one embodiment, the targeting composition binds to IGF2R at the amino acid sequence of SEQ ID NO: 6.

Moreover, SEQ ID NO: 6, binds with IGF2R in human cells and rat cells, which have amino acid of SEQ ID NO: 11 and SEQ ID NO: 12, respectively. These aspects of SEQ ID NO: 6 described with more detail below. Thus, the targeting composition including the amino acid sequence of SEQ ID NO: 6 targets and binds with IGF2R in human cells and rat cells. In further aspects, the targeting composition may bind to IGF2R associated with any tissue or cell in which IGF2R is highly expressed. Thus, because, IGF2R is highly expressed in fibrotic HSCs and in several cancers, the targeting peptide may bind with IGF2R associated with HSC, hepatocellular carcinoma tissues, melanoma cells, and brain cells.

In even more embodiments, an HSC targeting system is described that comprises a polypeptide comprising an amino acid sequence and is also configured to bind to at least a portion of an IGF2R associated with HSCs. In even further embodiments, the HSC targeting system may also include an agent.

In some embodiments, the HSC targeting system includes a polypeptide comprising the amino acid sequence of SEQ ID NO: 6 or an amino acid sequence with at least 70%, 80%, 90%, 95%, or 99% sequence identity to the amino acid sequence of SEQ ID NO: 6. In further aspects, the targeting composition may comprise the amino acid sequence of SEQ ID NO: 6 that includes L-amino acids. In further aspects, the targeting composition may comprise the amino acid sequence of SEQ ID NO: 6 that include D-amino acids.

In other embodiments, the polypeptide of the HSC targeting system comprises a dimer including a first and a second amino acid sequence, each of which includes either the amino acid sequence of SEQ ID NO: 6 or an amino acid sequence with at least 70%, 80%, 90%, 95%, or 99% sequence identity to the amino acid sequence of SEQ ID NO: 6. Moreover, the first and second amino acid sequences may be linked to one another via a linking moiety.

In further embodiments, the HSC targeting system may further include various agents such as an anti-fibrotic agent, an anti-cancer agent, a proapoptotic agent, or an imaging agent. Moreover, the agent may be attached to the polypeptide using conventional means known by those in the art, and thus, in some embodiments the agent is covalently attached to the polypeptide. Moreover, the attachment of the agent to the polypeptide may vary depending on the agent. For example, an anti-fibrotic agent may be covalently attached to the polypeptide via an attachment moiety. The use of an agent with these particular embodiments may be related to diagnosis, prevention, and/or treatment of various health disorders.

In event further embodiments, the HSC targeting system includes a targeting composition including a dimeric polypeptide comprising a first and second amino acid sequence, which may be linked to one another via a linking moiety. Additionally, the dimeric polypeptide is configured to bind to at least a portion of an IGF2R associated with HSCs. Moreover, both the first and the second amino acid sequences include either the amino acid sequence of SEQ ID NO: 6 or an amino acid sequence with at least 70%, 80%, 90%, 95%, or 99% sequence identity to the amino acid sequence of SEQ ID NO: 6.

In even further aspects, agents such as an anti-fibrotic agent, an anti-cancer agent, a proapoptotic agent, or an imaging agent are also included embodiments of the HSC targeting system involving a dimeric polypeptide. The agents may be attached to the dimeric polypeptide using conventional means known by those in the art, which include a covalent attachment to at least a portion of the dimeric polypeptide to the polypeptide. In some embodiments, an anti-fibrotic agent may be covalently attached to the dimeric polypeptide via a linking moiety that may include a lysine residue.

In additional embodiments, the targeting compositions and systems disclosed herein may be utilized in methods for treating numerous health disorders. As such, the binding of IGF2R and the agents may include further aspects that improve the methods of treatment.

Liver fibrosis is characterized by the excessive accumulation of extracellular matrix ("ECM") in the liver. During liver injury, HSCs are activated, which causes HSCs to multiply and to produce ECM and profibrogenic cytokines. Liver fibrosis may be reverted through antifibrotic therapy, by inhibiting the activation and proliferation of HSCs as well as ECM production. Thus, antifibrotic therapy, inhibiting HSCs is an effective treatment of liver fibrosis.

Therapeutic agents including small molecular antifibrotic molecules, oligonucleotides, and siRNA have been studied for treating liver fibrosis. For example, a siRNA was recently developed that inhibited the activation of HSCs. In order for the siRNA to exert its therapeutic effect with minimum toxicity, it must be specifically delivered to the target cells, HSC. However, due to the lack of drug delivery systems targeting the HSCs, antifibrotic therapy involving agents like siRNA is limited.

As previously discussed, IGF2R is expressed in HSCs and the expression is upregulated during liver fibrogenisis, making IGF2R a target for HSC specific drug delivery. The targeting composition and systems disclosed herein bind with IGF2R and include an attached agent. These compositions and systems may be utilized in treatment methods for liver fibrosis by delivering therapeutic agents to HSCs that inhibit their activation. Moreover, FIGS. 17A and 17B demonstrate the cellular uptake and FIG. 18 and FIG. 19 demonstrate the biodistribution of the anti-fibrotic agent siRNA when modified with Peptide-431 in comparison to other HSC specific delivery systems. As shown, Peptide-431 resulted in the highest cellular uptake of siRNA and well as the highest specificity for HSCs. This further illustrates that targeting compositions and systems described herein may be used in methods for treating liver fibrosis.

Embodiments of the present invention that are directed towards methods for treating liver fibrosis include the targeting compositions and systems that include an agent. Additionally, these embodiments further include pharmaceutically acceptable carriers that are capable of administering the agent. Thus, a method for treating liver fibrosis through the inhibition of HSCs may comprise administering a targeting composition or system with an attached agent, such that the targeting composition binds with IGF2R on HSCs, includes a pharmaceutically acceptable carrier, and may be administered orally.

The agent may include an anti-fibrotic agent including small molecular antifibrotic molecules, oligonucleotides, and siRNA. In some embodiments, the anti-fibrotic agent may include proapoptotic peptide KLAKLAKKLAKLAK (KLA) (SEQ ID NO: 13), which is used to induce cell death. The agent may be administered by any number of methods known to those of ordinary skill in the art including, but not limited to subcutaneous (subq), intravenous (I.V.), intraperitoneal (I.P.), orally, parenterally, etc. Additionally, to administer the targeting composition or targeting system including the attached agent may be formulated in conventional manners using one or more pharmaceutically acceptable carriers or excipients.

In embodiments, formulation materials may be used for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight peptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", 18'h Ed. (Gennaro, ed., Mack Publishing Company, Easton, Pa., 1990)).

In further embodiments, the present invention is also directed towards methods for treating other diseases. As discussed, the targeting compositions and systems disclosed herein may bind with IGF2R on other cells or tissues in which IGF2R is highly expressed. IGF2R was found to be highly expressed in several cancers including hepatocellular carcinoma (HCC) tissues and melanoma. Therefore, the targeting composition and systems disclosed may be utilized in methods for treating cancer. In addition, the expression level of IGF2R on the surface of lysosomes has been found to be high, and therefore, the targeting compositions and systems disclosed may also be utilized in methods for treating lysosomal storage diseases (LSDs).

Embodiments of the present invention that are directed towards methods for treating cancer and LSDs include the targeting compositions and systems that include an agent Additionally, these embodiments further include pharmaceutically acceptable carriers that are capable of administering the agent. Thus, a method for treating cancer may comprise administering a targeting composition or system with an attached anti-cancer agent, such that the targeting composition binds with IGF2R on cancer cells, includes a pharmaceutically acceptable carrier, and may be administered orally or via other conventional routes. A method for treating LSDs may comprise administering a targeting composition or system with an attached therapeutic agent, such that the targeting composition binds with IGF2R on lysosomal cells, includes a pharmaceutically acceptable carrier, and may be administered orally or via other conventional routes.

The anti-cancer agent includes any agents that are used in the treatment of cancer. The agent may be administered by any number of methods known to those of ordinary skill in the art including, but not limited to subcutaneous (subq), intravenous (I.V.), intraperitoneal (I.P.), orally, parenternaly, etc. Additionally, to administer the targeting composition or targeting system including the attached agent may be formulated in conventional manners using one or more pharmaceutically acceptable carriers or excipients disclosed above.

Figure 16A:
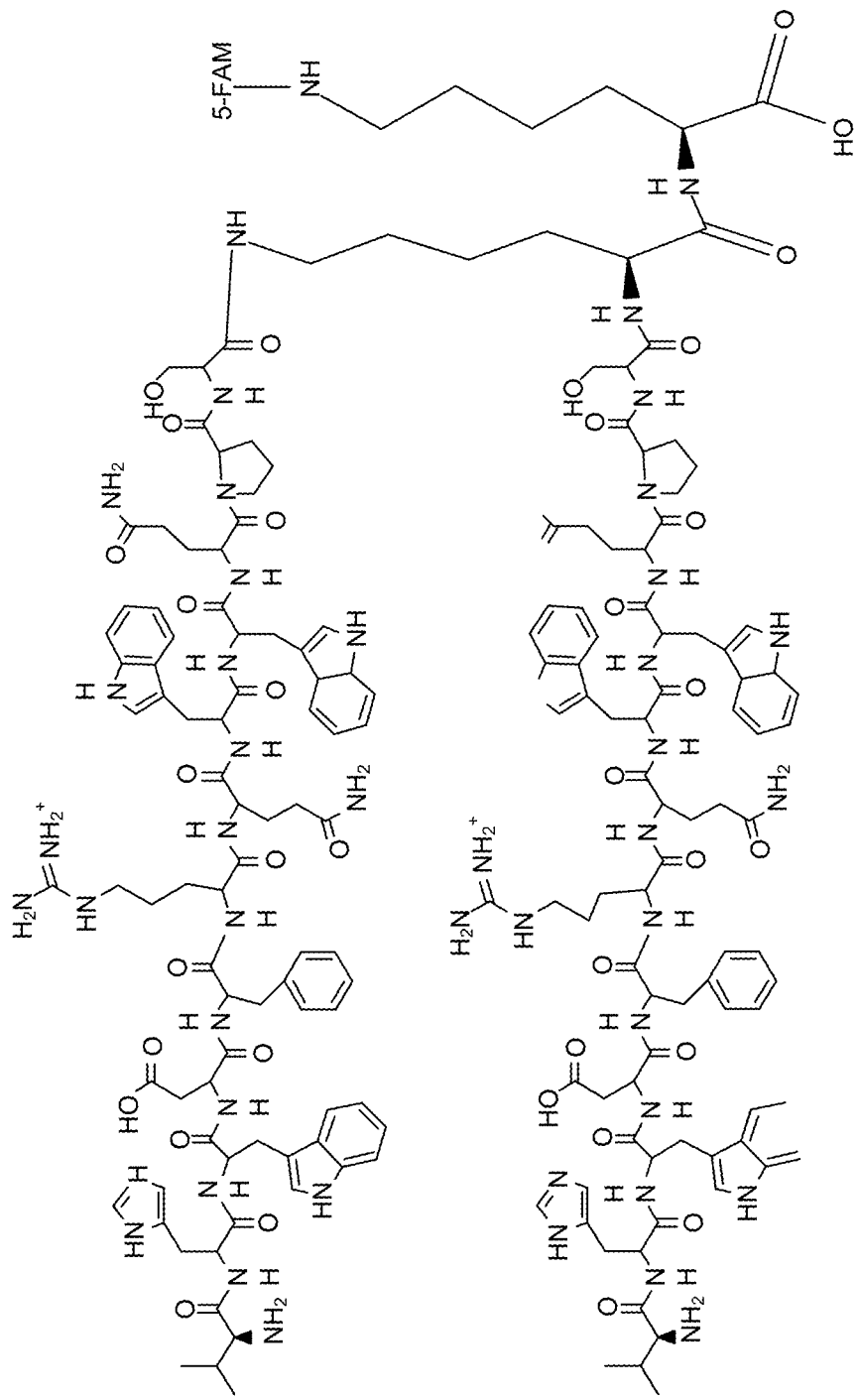
FIG. 16A shows an exemplary molecule, in which a dimer of Peptide-431 is linked via a lysine and an imaging agent is coupled to the linker.

In further embodiments that include Peptide-431 or the amino acid of SEQ ID NO: 6, the targeting composition or system may be modified to improve or later the targeting of IGF2R. In some embodiments, two copies of Peptide-431 or the amino acid of SEQ ID NO: 6 may be used. The two copies may be linked to one another via a linking moiety, which may include lysine. As a result, a dimeric Peptide-431 or a dimeric amino acid of SEQ ID NO: 6 may be formed. An exemplary molecule including a dimerized Peptide-431 linked by lysine is shown in FIG. 16A. In further aspects, binding affinity of dimeric variations improved by 9-fold in comparison to the monomeric version. These aspects discussed in more detail in the Example section below.

In additional aspects, any embodiment including the targeting may comprise any one of the amino acid sequences of SEQ ID NOS: 1-10. Further, any embodiment including the targeting composition may comprise an amino acid with at least 70%, 80%, 90%, 95%, or 99% sequence identity to any one of the amino acid sequences of SEQ ID NOS: 1-10. In further aspects, any embodiments including the HSC targeting system may include one or more polypeptides comprising an amino acid sequence with at least 70%, 80%, 90%, 95%, or 99% sequence identity to any one of the amino acid sequences of SEQ ID NOS: 1-10.

In even more embodiments, the targeting composition may include one or more polypeptides. In certain aspects, the one or more polypeptides comprises an amino acid having at least at least 70%, 80%, 90%, 95%, or 99% sequence identity to any one of the amino acid sequences of SEQ ID NOS: 1-10. Further, the one or more polypeptides may comprise an amino acid having a least 70%, 80%, 90%, 95%, or 99% sequence identity to the amino acid sequence of SEQ ID NO: 1. The one or more polypeptides may comprise an amino acid having a least 70%, 80%, 90%, 95%, or 99% sequence identity to the amino acid sequence of SEQ ID NO: 2. The one or more polypeptides may comprise an amino acid having a least 70%, 80%, 90%, 95%, or 99% sequence identity to the amino acid sequence of SEQ ID NO: 3. The one or more polypeptides may comprise an amino acid having a least 70%, 80%, 90%, 95%, or 99% sequence identity to the amino acid sequence of SEQ ID NO: 4. The one or more polypeptides may comprise an amino acid having a least 70%, 80%, 90%, 95%, or 99% sequence identity to the amino acid sequence of SEQ ID NO: 5. The one or more polypeptides may comprise an amino acid having a least 70%, 80%, 90%, 95%, or 99% sequence identity to the amino acid sequence of SEQ ID NO: 6. The one or more polypeptides may comprise an amino acid having a least 70%, 80%, 90%, 95%, or 99% sequence identity to the amino acid sequence of SEQ ID NO: 7. The one or more polypeptides may comprise an amino acid having a least 70%, 80%, 90%, 95%, or 99% sequence identity to the amino acid sequence of SEQ ID NO: 8. The one or more polypeptides may comprise an amino acid having a least 70%, 80%, 90%, 95%, or 99% sequence identity to the amino acid sequence of SEQ ID NO: 9. The one or more polypeptides may comprise an amino acid having a least 70%, 80%, 90%, 95%, or 99% sequence identity to the amino acid sequence of SEQ ID NO: 10.

In even further aspects, any one of the polypeptides or amino acid sequences included as part of the targeting composition, the HSC targeting system, or the various treatment methods, can bind to IGFR2 protein or amino acid sequence having at least 70%, 80%, 90%, 195%, or 99% sequence identity to any one of amino acid sequences of SEQ ID NO: 11 and SEQ ID NO: 12.

In even further embodiments, any of the amino acids included in the targeting composition or targeting system may be substituted on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Amino acid substitutions may alternatively be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other, embodiments amino acid substitutions that are within ±1 are included, and in yet other embodiments amino acid substitutions within ±0.5 are included.

Some embodiments of the present invention are directed towards a method, depicted in FIG. 1, for identifying a specific peptide. At a high level, the method involves a combinatorial phage biopanning procedure that combines protein-based biopanning with cell-based biopanning. Conventional protein-based biopanning is conducted in a controlled environment without interference and thus, adequately identifies high specificity peptides. However, a recombinant protein may have a different conformation from its native structure on the cells. Therefore, peptides identified from protein-based biopanning may not bind to the same target on a cell. By contrast, peptides identified from cell-based biopanning can effectively bind to the native target on the cells. The disadvantage of cell-based biopanning is that there are many other proteins, lipids, and carbohydrates on the cell surface, leading to interference with the phage biopanning. By combining these techniques, a peptide may be identified that exhibits high specificity to a given target and also exhibits binding affinity with the same target when it is on a cell.

Specifically, the method includes a first step of conducting a combinatorial phage biopanning procedure comprising multiple rounds. Protein-based biopanning is conducted in the first, third, and fifth rounds, while cell-based biopanning is conducted in the second and fourth rounds. Next, phage clones, which are randomly selected after the fourth and fifth rounds, undergo amplification and DNA sequencing. The binding affinity of the selected phage clones are then evaluated by ELISA. Peptides are then synthesized from the peptide encodings of the phages with the highest binding affinity. The specificity of the synthesized peptides is then evaluated based on cellular uptake. Lastly, a peptide with the greatest binding affinity and highest specificity may be identified by comparing each peptide's binding affinity and specificity.

Other embodiments describe employing the above method to identify polypeptides that target the IGF2R on hepatic stellate cells in humans and rats. As illustrated in FIG. 1, the combinatorial phage biopanning procedure was conducted using recombinant human IGF2R extracellular domain protein (the first, third, and fifth rounds) and rat hepatic stellate cells HSC-T6 (the second and fourth rounds). After each round, unbound phages were removed while bound phages were recovered and amplified for the next round of biopanning. Twenty-eight phage clones were randomly selected after the fourth and fifth rounds of biopanning.

Figures 3A, 3B:
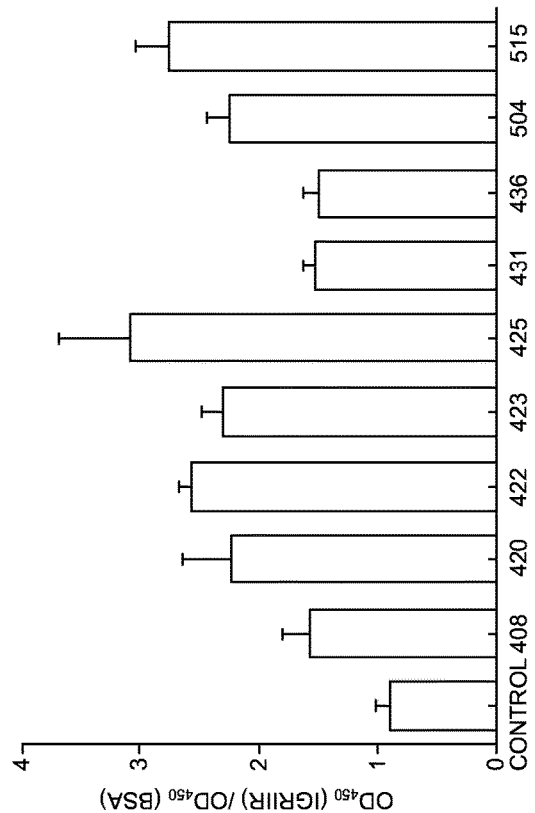
FIG. 3A shows peptide sequences encoded by phages randomly selected after the fourth and fifth rounds of the biopanning procedure illustrated in FIG. 1.
FIG. 3B depicts binding affinity of the randomly selected phage clones evaluated by ELISA on human recombinant IGF2R protein.
Figure 4B:
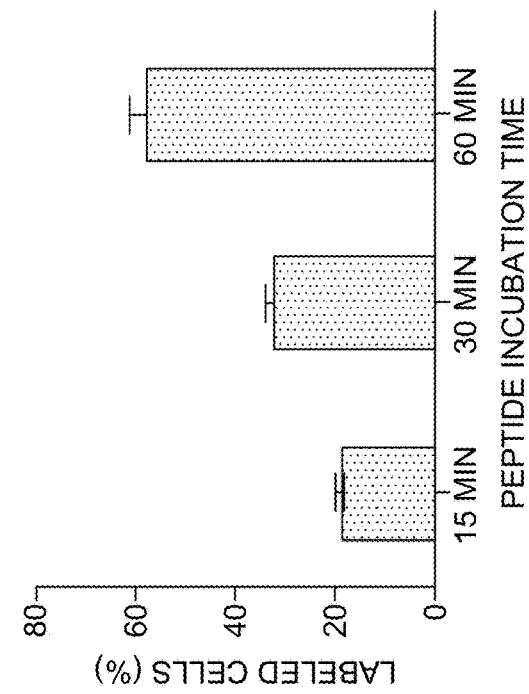
FIGS. 4A-4B show effects of cell detachment method and incubation time on cellular uptake of the identified peptides.
Figure 4A:
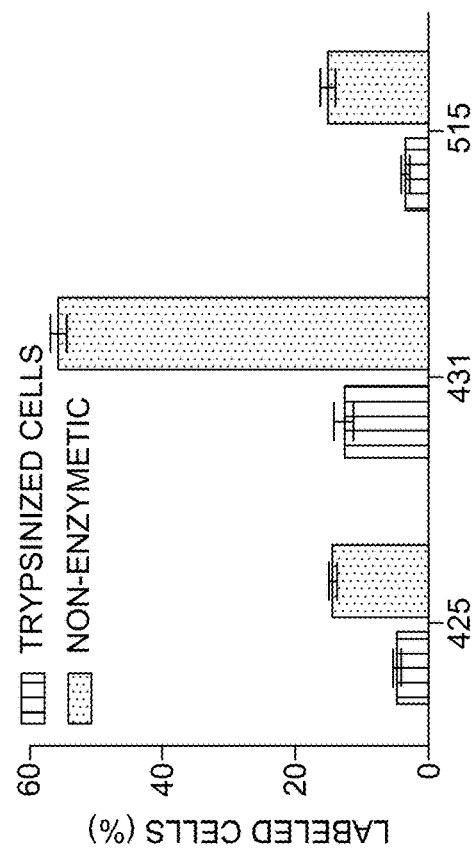
Figure 5C:
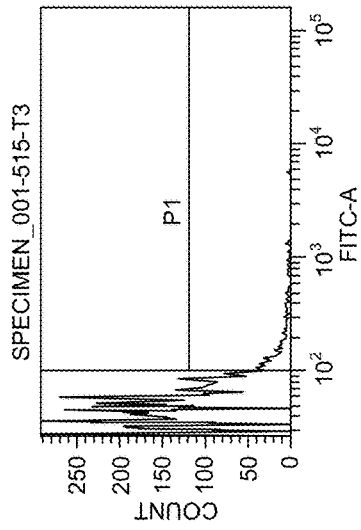
FIGS. 5A-5F show effects of cell detachment on cellular uptake of the identified peptides.
Figure 5B:
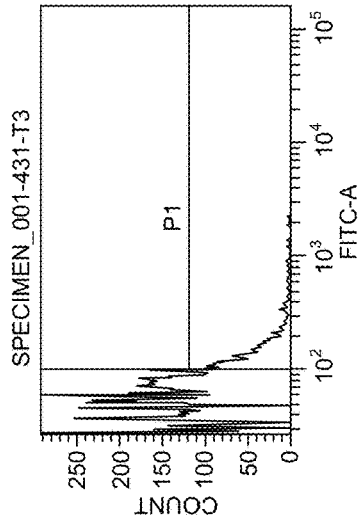
Figure 5A:
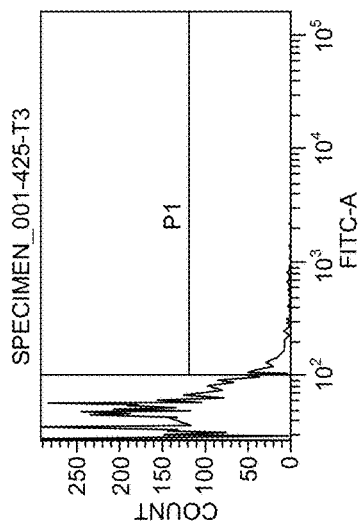
Figure 5F:
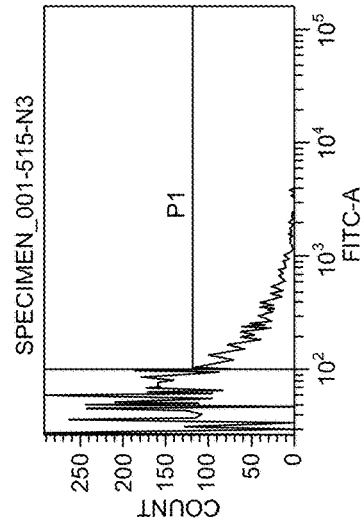
Figure 5E:
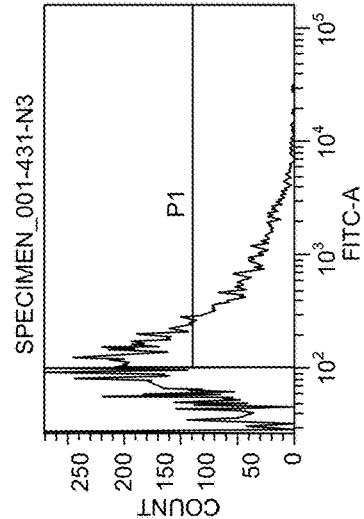
Figure 5D:
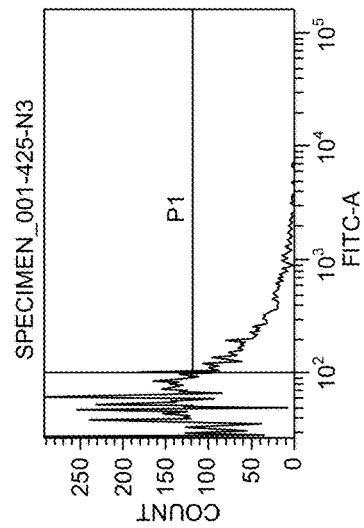
Figure 6B:
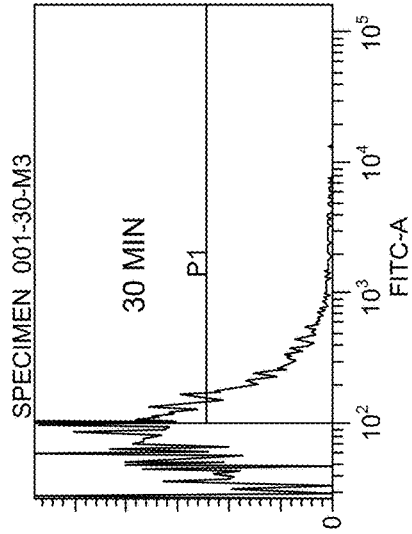
FIGS. 6A-6C show effects of incubation time on cellular uptake of an identified peptide (Peptide-431)
Figure 6A:
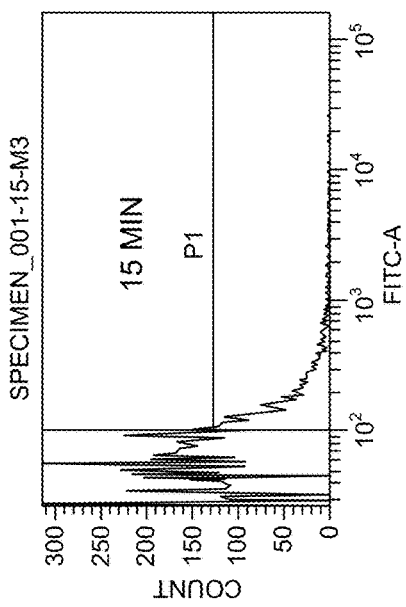
Figure 6C:
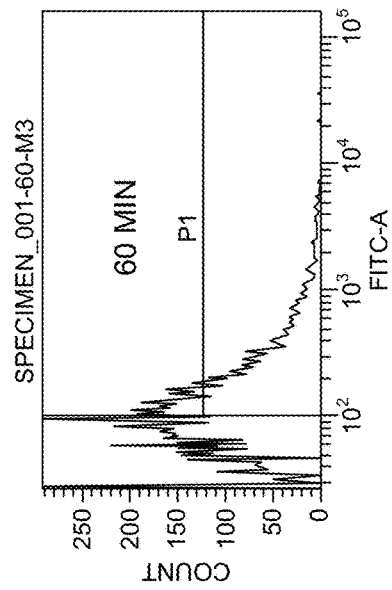
Figure 7A:
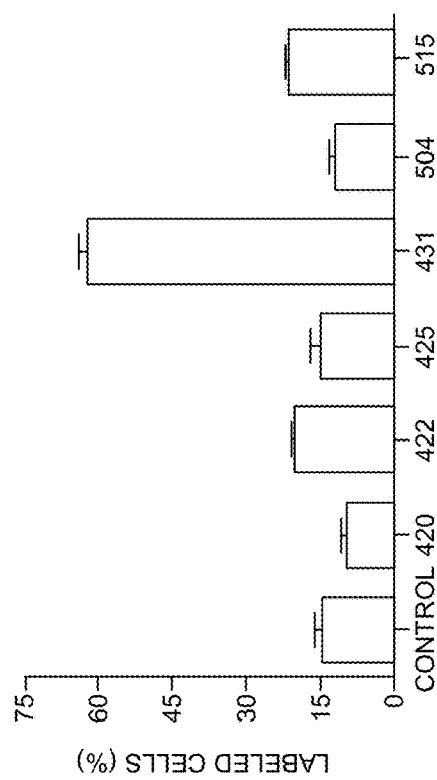
FIGS. 7A-7B show cellular uptake of identified peptides in human hepatic stellate cells (LX-2 cells) and rat hepatic stellate cells (HSC-T6 cells)
Figure 7B:
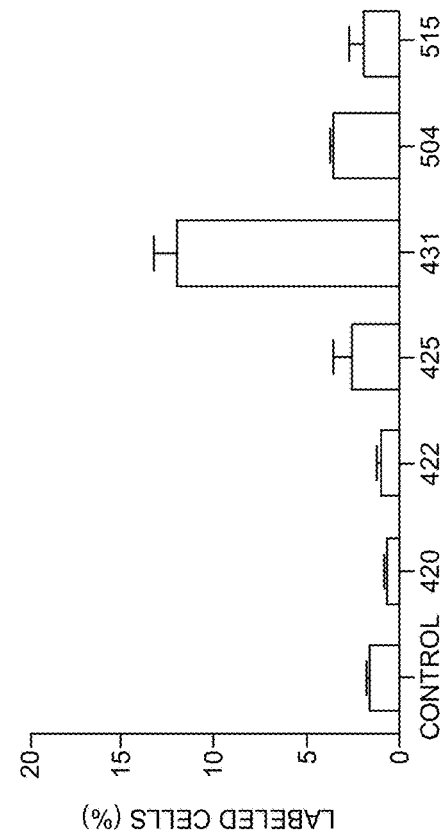
Figure 8G:
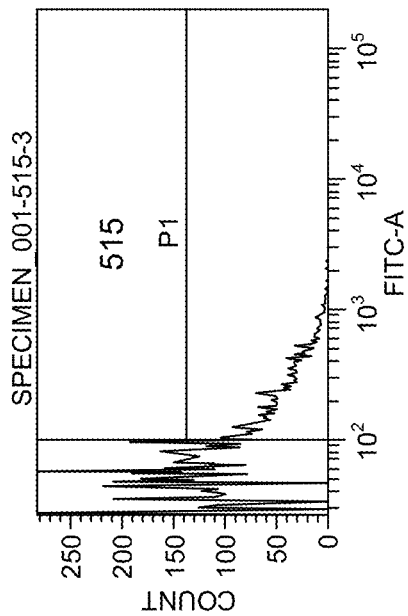
Figure 8F:
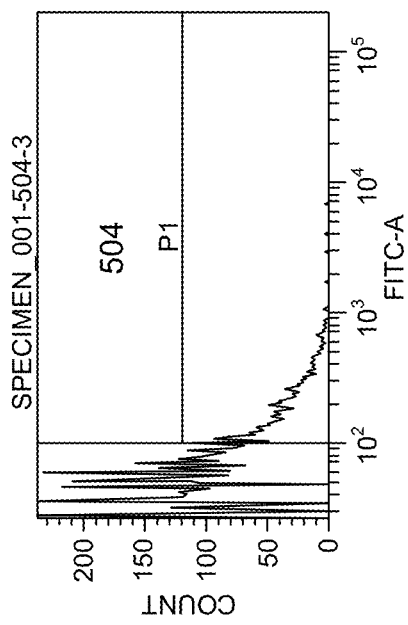
Figures 9A, 9B, 9C:
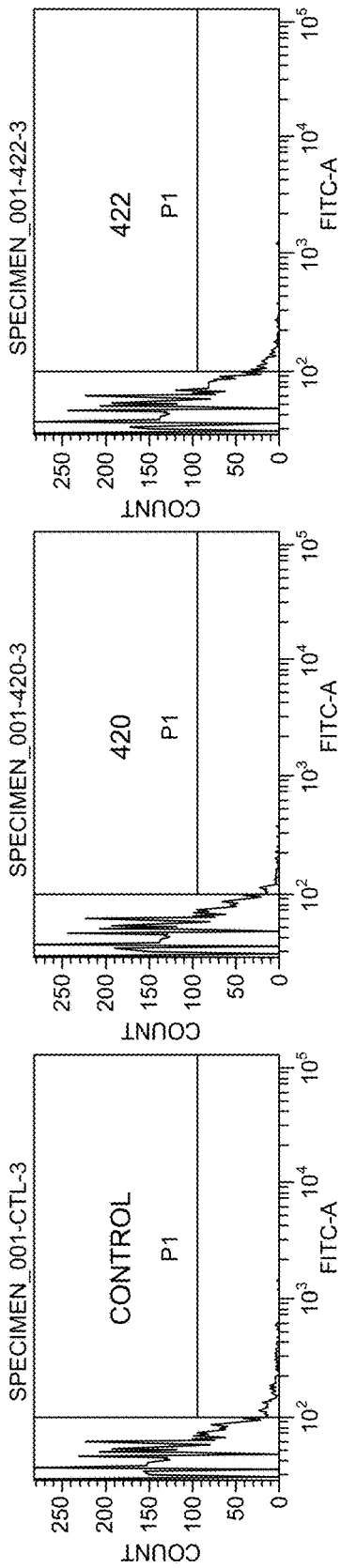
FIGS. 9A-9G show cellular uptake of identified peptides in HSC-T6 cells.
Figure 9D:
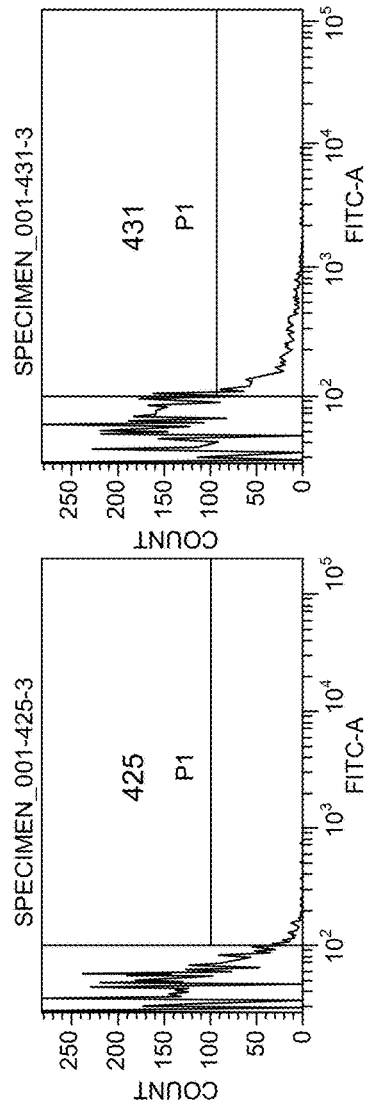
Figure 9E:
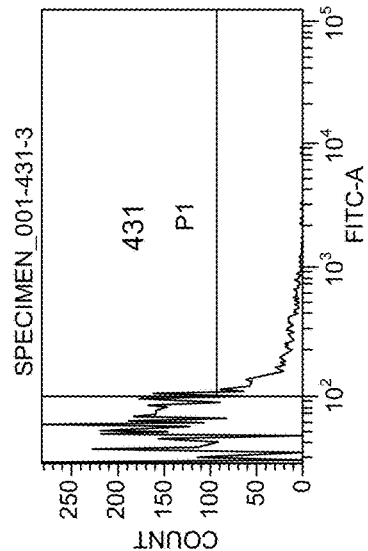
Figure 9G:
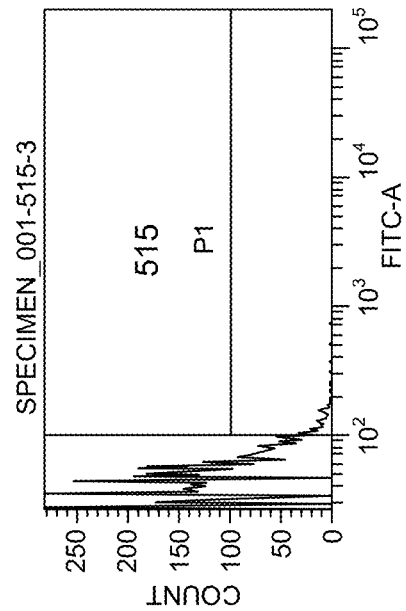
Figure 9F:
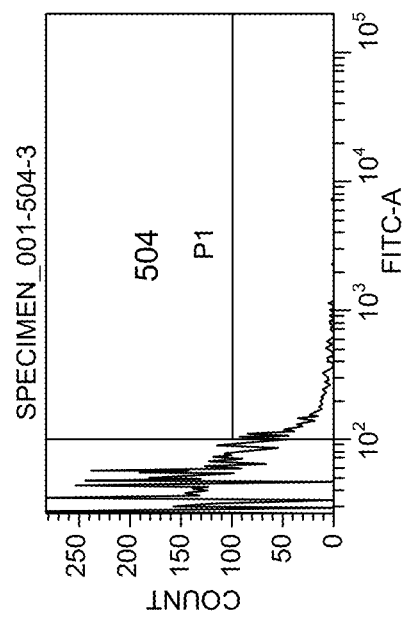

The DNA of each phage was extracted, purified, and sequenced with an ABI Genetic Analyzer 3100 (Applied Biosystems, USA). In more specific aspects, the primer used for sequencing was 5'-CCCTCATAGTTAGCGTA ACG-3', SEQ ID NO: 14, and the encoded peptide sequences of the phages were deduced from the DNA sequence. FIG. 3A shows identified peptide sequences, and their frequency of occurrence. The following peptide sequences were derived from the twenty-eight phage clones, which include the respective SEQ. ID No: of the amino acid sequence:

"GFPTRFEALSSN", SEQ ID NO: 1

"GLHTSATNLYLH", SEQ ID NO: 2

"HSFKWLDSPRLR", SEQ ID NO: 3

"SGVYKVAYDGQH", SEQ ID NO: 4

"KASGSPSGFWPS", SEQ ID NO: 5

"VHWDFRQWWQPS", SEQ ID NO: 6

"RRVDKVQYDRQH", SEQ ID NO: 7

"GLHTSALSDLH", SEQ ID NO: 8

"HTSSLWHLFRST", SEQ ID NO: 9
and

"SGVYKVAYDWQH". SEQ ID NO: 10

The binding affinity of the twenty-eight phages was evaluated by ELISA on recombinant human IGF2R protein. FIG. 3B shows the binding efficacy associated with each of the peptide sequences derived from the phage clones. Each of these sequences were able to bind with IGF2R, but only the six phage clones showing the highest binding affinity were then used to synthesize their encoded peptides in order to undergo further affinity and specificity studies in human and rat cells, which are depicted in FIGS. 4A-4B, 5A-5F, 6A-6C, 7A-7B, 8A-8G, 9A-9G, and 10A-10C. As shown, Phage No. 431 with the peptide sequence of SEQ ID NO: 13, "VHWDFRQWWQPS" ("Peptide-431") exhibited the greatest binding affinity and highest specificity and was identified as a polypeptide than can be used to target IGF2R on hepatic stellate cells in humans and rats. Additionally, the particular embodiment may include more specific aspects related to the materials and techniques employed by this method, which are described with more detail in the Experiment section below.

Further embodiments of the present invention relate to various uses and applications of the Peptide-431 identified by the foregoing methods. The embodiments include Peptide-431 as part of the targeting compositions or the HSC targeting system disclosed herein. In such instances, Peptide-431 binds to IGFR2 on the surface of HSCs and is able to deliver various agents to the targeted cells including proapoptotic agents, antifibrotic agents, anti-cancer agents, or imaging agents. In even more embodiments, a dimer of the Peptide-431 identified by the foregoing methods may alternatively be used as part of the targeting compositions or the HSC targeting system disclosed herein.

EXAMPLES

To demonstrate the accuracy in which the peptides were selected and identified, descriptions of experiments that were conducted, and their respective results are provided herein. Furthermore, additional experiments were conducted to illustrate the targeting and delivery properties of Peptide-431, which includes the amino acid sequence of SEQ ID NO: 6. Descriptions of those experiments and their results are also provided.

At a high level, protein- and whole cell-based phage display biopannings were conducted to identify phage/peptide candidates. Phage ELISA, cellular uptake, and cell viability assay were employed to evaluate the binding affinity and specificity of these peptide ligands to recombinant human IGF2R and HSCs. IGF2R siRNA was used to silence the IGF2R protein expression in human hepatic stellate cells (LX-2) to confirm the specificity of the identified peptide ligands. Among the identified peptide candidates, peptide-431 shows the highest binding affinity and specificity to recombinant human IGF2R protein and HSCs. The apparent dissociation constant (Kd) of peptide-431 is 6.19 μM for LX-2 cells and 12.35 μM for rat hepatic stellate cells HSC-T6. Cellular uptake of peptide-431 in LX-2 cells is significantly reduced after silencing IGF2R with siRNA. Peptide-431 also enhances the uptake of a proapoptotic peptide (KLA peptide) in LX-2 and HSC-T6 cells, indicating that peptide-431 can be used as a targeting ligand to deliver antifibrotic agents into not only rat but also human HSCs. Dimerization of peptide-431 further increase its binding affinity to LX-2 cells by approximately 9-fold.

Phage Display Biopanning

Figure 2:
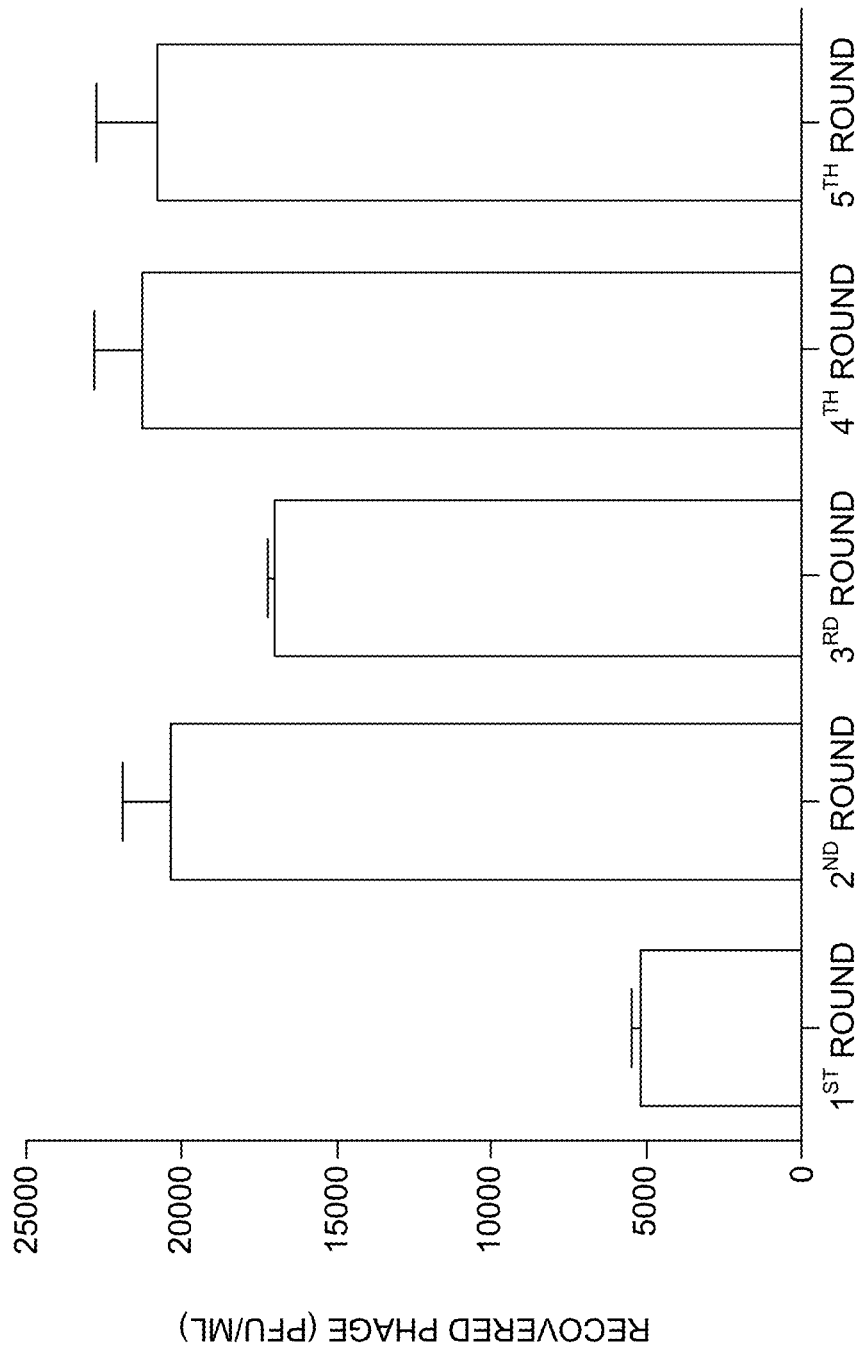
FIG. 2 depicts the number of recovered phages after each round of the combinatorial phage biopanning procedure illustrated in FIG. 1.

A combinatorial phage biopanning procedure was conducted using recombinant human IGF2R extracellular domain protein (the first, third, and fifth rounds) and rat hepatic stellate cells HSC T6 (the second and fourth rounds) as shown in FIG. 1. Briefly, $1\times10^{11}$ pfu phages from the Ph.D. 12 phage library were incubated with immobilized IGF2R protein in a 24 well plate at 4° C. for 2 h under shaking. Unbound phages were removed by washing the immobilized IGF2R protein with PBST (0.1% Tween 20) three times. Bound phages were recovered by adding 1 mL of elution buffer (0.2 M glycine HCl, pH 2.2) and then neutralized with 150 pL of 1 M Tris HCl (pH 9.1). The recovered phages were then amplified for the next round of biopanning. The whole cell biopanning was performed as previously reported. Briefly, HSC T6 cells were detached with ice cold PBS containing 5 mM EDTA and then suspended in DMEM medium containing 1% BSA at a density of 1×107 cells/mL. $2.0\times10^{10}$ phages from the previous round were incubated with the cells at 4° C. for 1 h under shaking. After incubation, 200 pL of organic phase composed of dibutylphthalate and cyclohexanol (9:1, v/v) was added to the cell suspension and centrifuged at 4° C. for 10 min. The bottom of the microcentrifuge tube, which contains the cell/phage complex, was cut off after snap freezing in liquid nitrogen. The bound phages were recovered by infecting ER2738 bacterial cells, followed by amplification for next round biopanning. FIG. 2 shows the number of recovered phages after each round.

Phage DNA Sequencing and Phage ELISA

Twenty eight phage clones were randomly selected after the fourth and fifth rounds of biopanning and cultured in 1 mL of ER2738 bacteria (growing in early stage) at 37° C. for 4.5 h. Phage DNA was extracted, purified using the DNA clean system (Promega, Madison, Wis.), and then sequenced with an ABI Genetic Analyzer 3100 (Applied Biosystems, USA). The primer used for sequencing is SEQ ID NO: 14, 5'-CCCTCATAGTTAGCGTA ACG-3'. As shown in FIG. 3A, 16 of the selected phages encode the same peptide sequence, which referred to as peptide 515. One of the phages was peptide insertless. In FIG. 3B, binding affinity of the selected phage clones encoding inserted peptides was evaluated by ELISA on recombinant human IGF2R protein. Compared to the control phage, which is peptide insertless, all the selected phages exhibited higher binding affinity.

Cellular Uptake of Selected Peptides and Binding Affinity

The six phages (420, 422, 425, 431, 504, and 515) which showed the highest binding affinity to the IGF2R protein were used to synthesize the encoded peptides for affinity studies in human and rat hepatic stellate cells. We examined cellular uptake of 5 FAM labeled peptides (425, 431, and 515) in human hepatic stellate cells LX 2 upon treatment with nonenzymatic cell dissociation solution and trypsin. All three peptides exhibited higher cellular uptake in nonenzymatic cell dissociation solution, which is consistent with a previous report. We also evaluated the effect of incubation time on cellular uptake of the peptides. 5 FAM labeled peptide 431 was incubated with LX 2 cells for different incubation time points. Cellular uptake of the peptide exhibited a time dependent increase. Therefore, nonenzymatic cell dissociation solution and 1 h incubation time were selected to evaluate all the peptides (420, 422, 425, 431, 504, and 515) in human hepatic stellate cells LX 2 and rat hepatic stellate cells HSC T6. On both cell lines, peptide 431 exhibited the highest binding affinity compared to the control peptide and other selected peptides. In addition, peptide 431 showed much higher cellular uptake in LX 2 (62%) than HSC 6 (12%) cells.

Figures 10A, 10B, 10C:
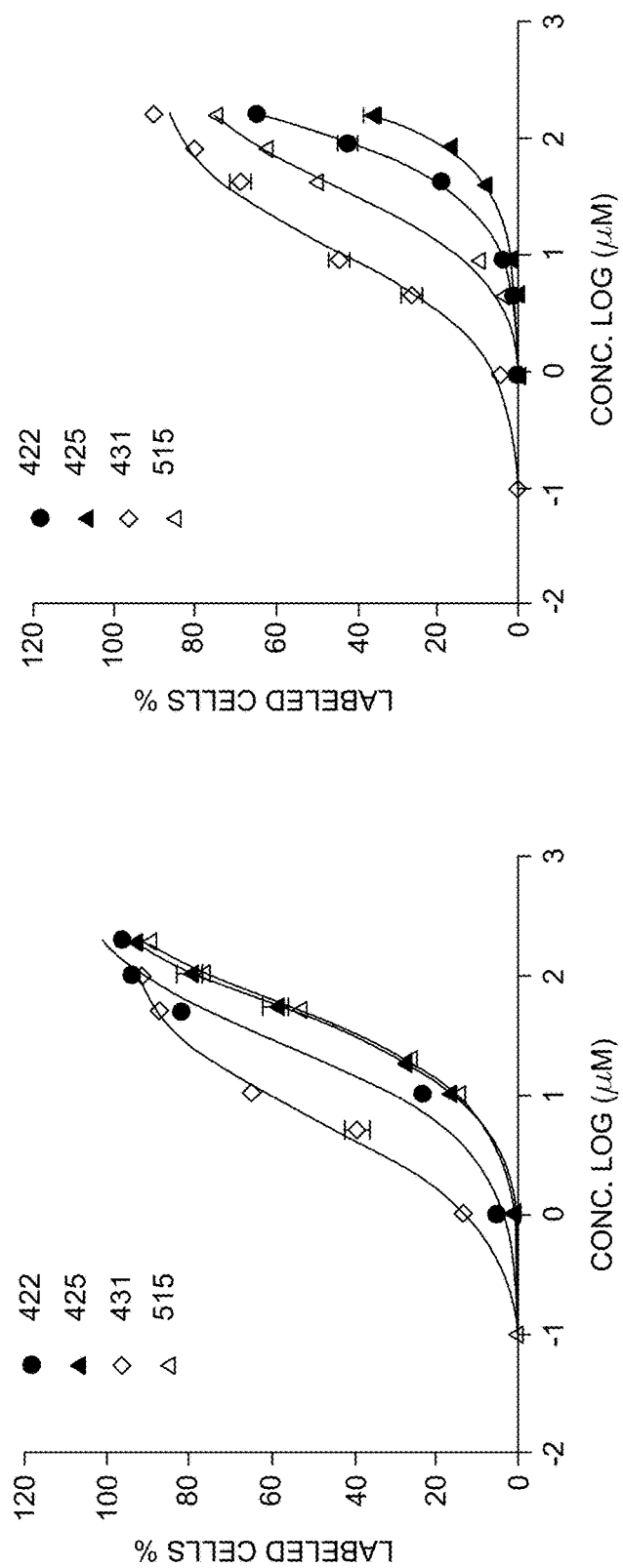
FIGS. 10A-10C depict apparent equilibrium dissociation constants (Kd) of identified peptides in LX-2 and HSC-T6 cells.

We next measured the apparent equilibrium dissociation constants (Kd) of the peptides (422, 425, 431, and 515) to LX 2 and HSC T6 cells as shown in FIG. 10A and FIG. 10B, respectively. The cells were incubated with 5 FAM labeled peptides at different concentrations for 1 h at 37° C. The labeled cells were detected by flow cytometry, and the apparent Kd value was calculated using GraphPad Prism. As demonstrated in FIGS. 10A-10C, peptide 431 showed the lowest apparent Kd (6.19 µM) in LX 2 cells. It also showed a comparable Kd (12.35 µM) in HSC T6 cells, suggesting its promising potential as a targeting ligand for both preclinical animal study and future clinical evaluation. The other three peptides (422, 425, and 515) also showed good binding to LX 2 cells. The result is consistent with the cellular uptake result depicted in FIGS. 7A-7B, 8A-8G, and 9A-9G.

Specificity of the Peptide 431 to IGF2R

Figure 11B:
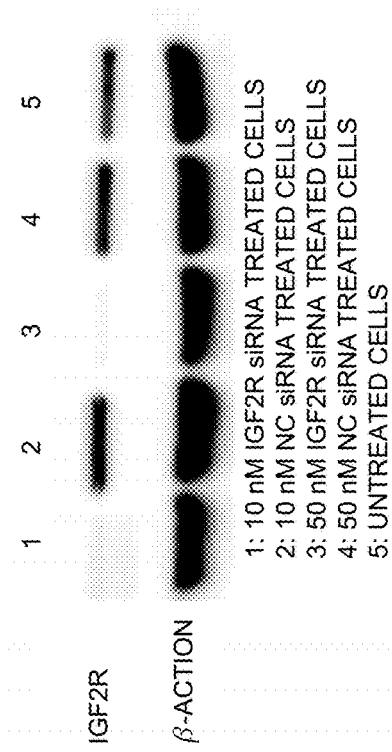
FIGS. 11A-11B depict an evaluation of the specificity of Peptide-431 to IGF2R in LX-2 cells.
Figure 11A:
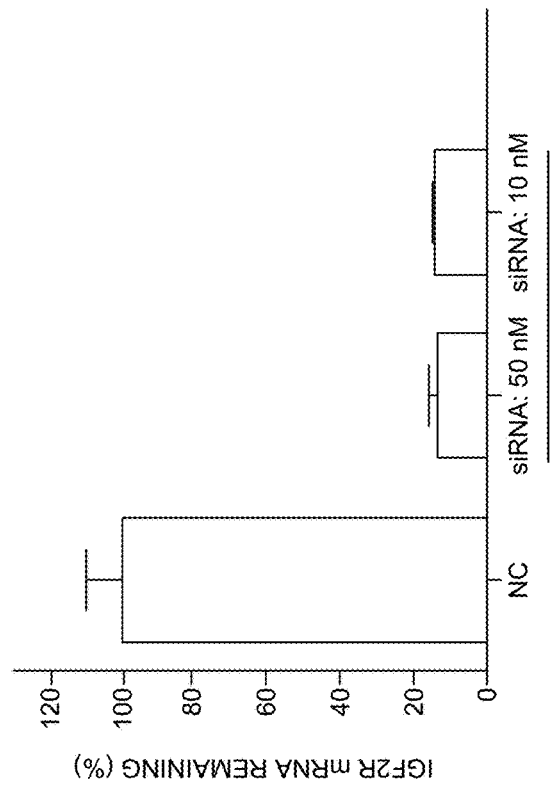
Figure 12A:
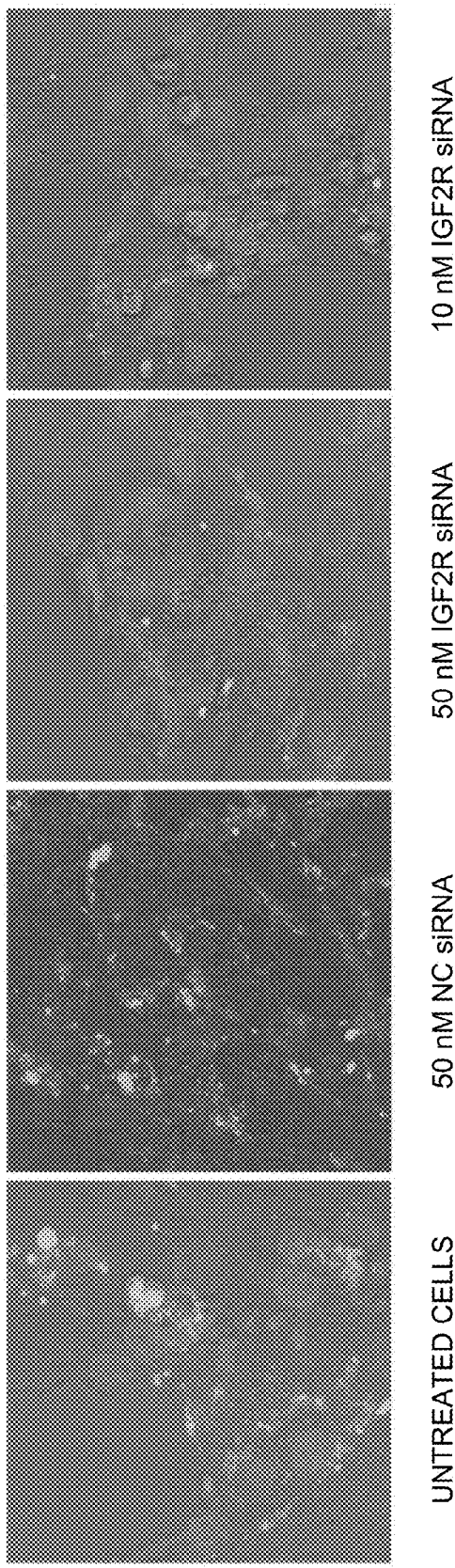
FIGS. 12A-12B depict additional evaluations of the specificity of Peptide-431 to IGF2R in LX-2 cells.
Figure 12B:
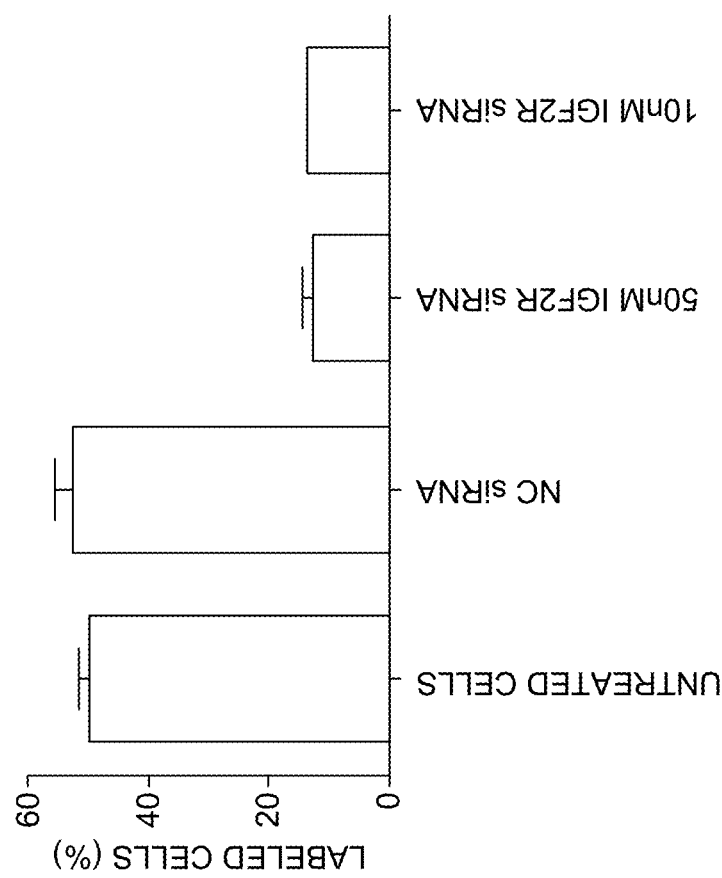
Figure 13A:
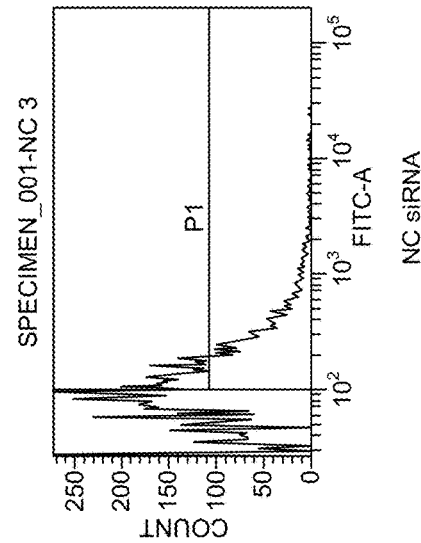
FIGS. 13A-13D depict additional evaluations of the specificity of Peptide-431 to IGF2R in LX-2 cells.
Figure 13B:
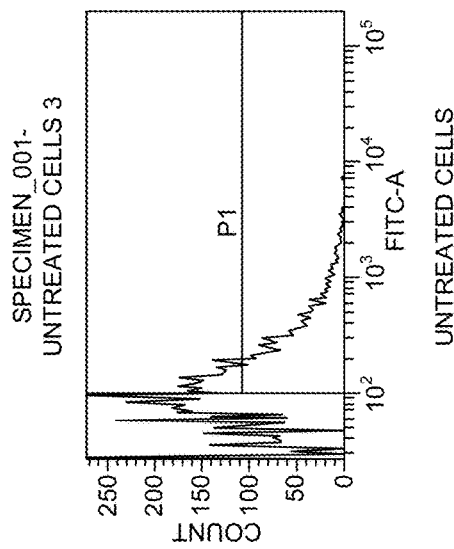
Figure 13C:
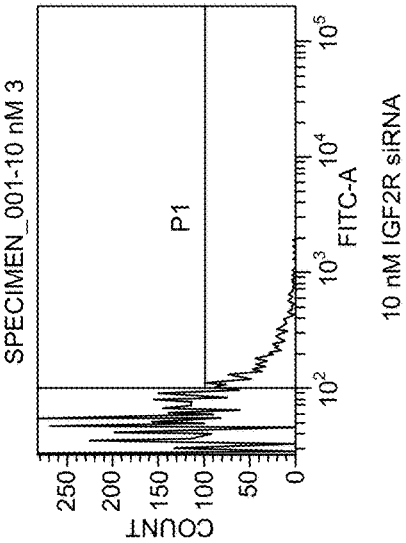
Figure 13D:
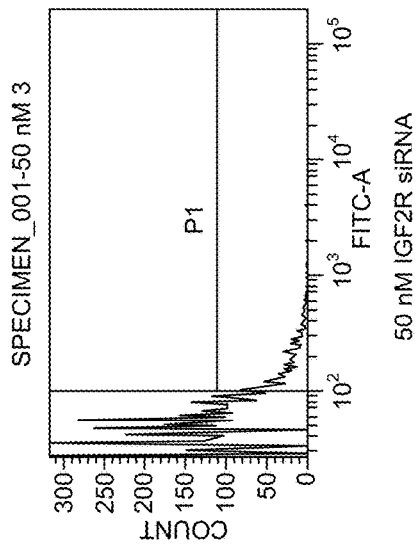

In addition to affinity, we also evaluated the specificity of peptide 431 to IGF2R in LX 2 cells. For this purpose, the expression of IGF2R in LX 2 cells was silenced using siRNA As shown in FIGS. 11A-11B, the IGF2R siRNA (10 and 50 nM) dramatically knocked down the expression of IGF2R in LX 2 cells at the mRNA and protein levels. After transfection with the siRNA for 24 h, the mRNA expression of IGF2R was silenced by more than 85%, and the protein expression was silenced to almost negligible levels. Accordingly, the IGF2R siRNA treated cells exhibited lower uptake of the 5 FAM labeled peptide 431 than the cells treated with scrambled siRNA, which is depicted in FIGS. 12A-12B. This result suggests high specificity of peptide 431 to IGF2R on LX 2 cells.

Serum Protein Binding Study

Figure 14:
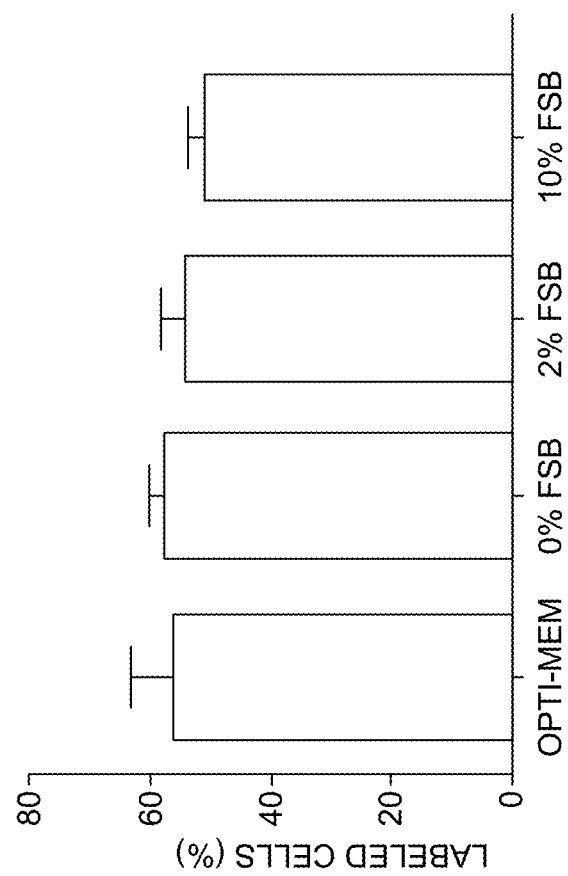
FIG. 14 illustrates the effects of FBS on cellular uptake of Peptide-431.

It is important to evaluate the stability of peptides in the presence of serum proteins, which may nonspecifically bind to IGF2R specific peptides. As a result, we evaluated the cellular uptake of 5 FAM labeled peptide 431 in LX 2 cells in the serum reduced medium OptiMEM and DMEM media containing different concentrations of FBS. As depicted in FIG. 14, cellular uptake of peptide 431 was not significantly affected by the FBS up to 10%, indicating good stability of the peptide in the presence of serum protein.

Cell Viability Assay

LX 2 and HSC T6 (1×104 cells per well) cells were cultured in 96 well plates for 12 h in DMEM medium containing 10% FBS. The peptide 431/KLA fusion peptide, the mixture of peptide 431 and KLA peptide, and KIA peptide were incubated with the cells for 48 h. Cell viability was measured using MTT (3 (4,5 dimethylthiazol2 yi) 2,5 diphenyltetrazolium bromide) assay.

Enhancement of the Uptake and Apoptotic Effect of a Proapoptotic Peptide

Figure 15A:
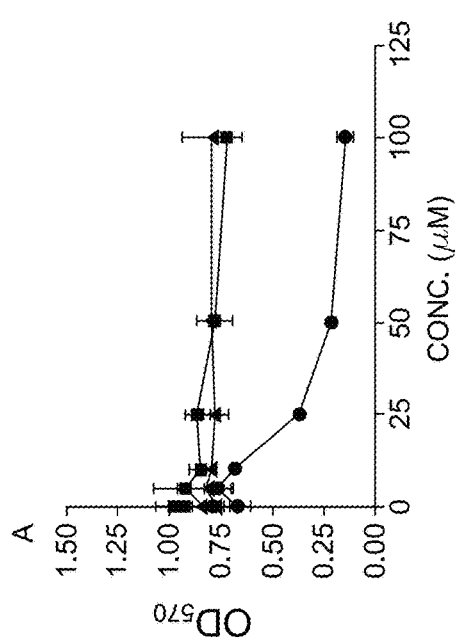
FIGS. 15A-15B depict the enhancements provided by Peptide-431 on the uptake and apoptotic effect of a proapoptotic peptide in LX-2 and HSC-T6 cells.
Figure 15B:
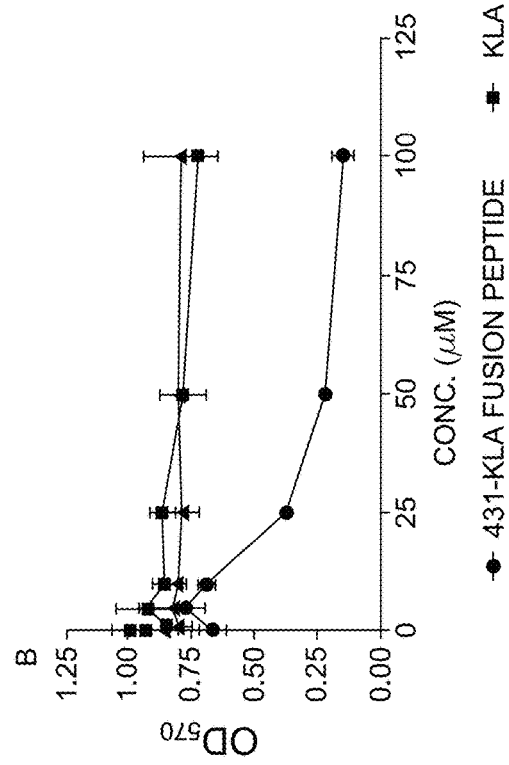

The proapoptotic peptide having the sequence of SEQ ID NO: 13, KLAKLAKKLAKLAK (KLA), is able to trigger mitochondrial disruption and induce cell death. However, the KLA peptide itself cannot enter cells to exert its proapoptotic activity. We therefore prepared a KLA/peptide 431 fusion peptide and examined its proapoptotic activity in LX 2 and HSC T6 cells. As depicted in FIG. 15A, the KLA peptide alone did not exhibit apoptotic activity due to its inability to enter the cells by itself. Similarly, the mixture of KLA and peptide 431 also did not exhibit apoptotic activity in LX 2 cells. By contrast, the KIA/peptide 431 fusion peptide induced significant cell death in LX 2 cells, indicating that peptide 431 mediates the cellular uptake of the fusion peptide in LX 2 cells. Similar results were observed in HSC T6 cells, which are depicted in FIG. 15B. These results clearly suggest the promising potential of using peptide 431 as a targeting ligand to mediate cellular uptake of therapeutic agents.

Dimerization of Peptide-431 Improves its Binding Affinity

Figure 16B:
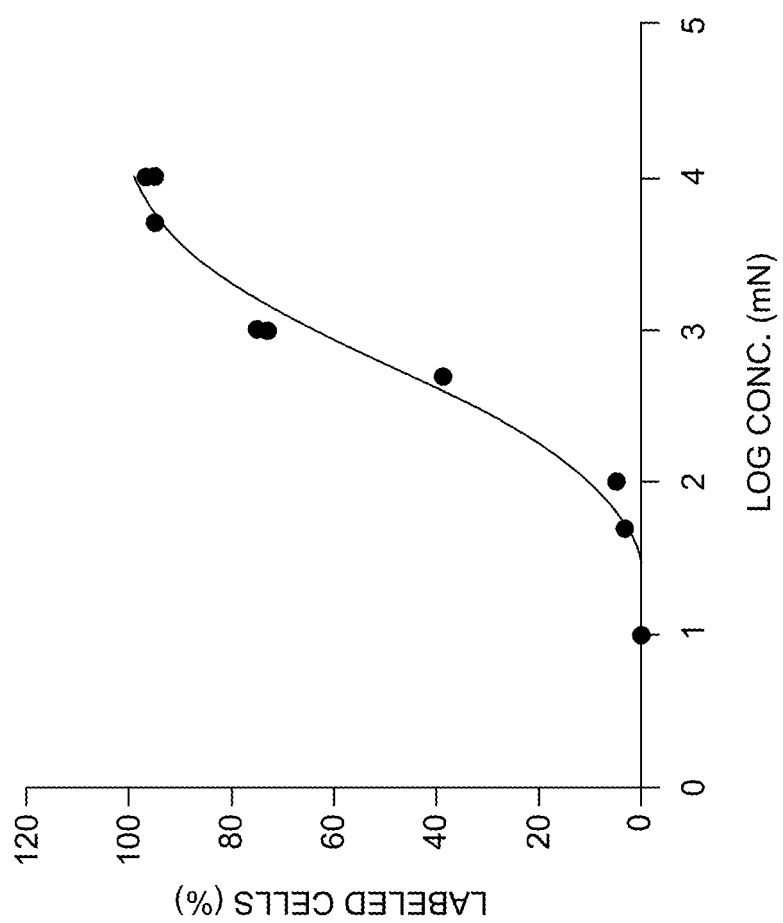
FIG. 16B depicts an equilibrium dissociation curve of the dimer of Peptide-431 in LX-2 cells.

In order to improve the binding affinity of peptide 431, two peptide 431, which may have the molecular structure depicted in FIG. 16A. Affinity of the dimeric peptide 431 was evaluated in LX 2 cells as described above. As shown in FIG. 16B, the apparent Kd value of the dimeric peptide 431 is 700.9 nM, which is approximately 9 fold lower compared to the monomeric peptide 431. This result is in agreement with a previous observation in which a dimeric peptide improves its binding affinity to prostate specific membrane antigen (PSMA).

Figure 17B:
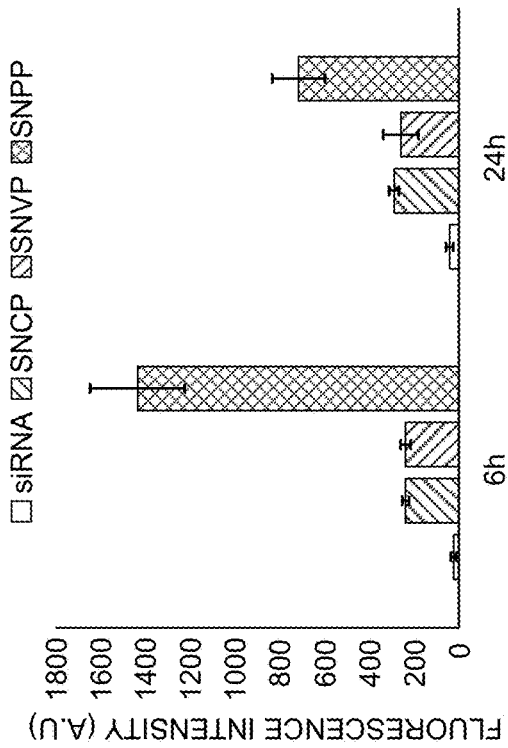
FIGS. 17A-17B depict cellular uptake of free siRNA and siRNA nanocomplexes modified with cholesterol (SNCP), Vitamin A (SNVP), and Peptide-431 (SNPP) in HSC-T6 cells and LX-2 cells.
Figure 17A:
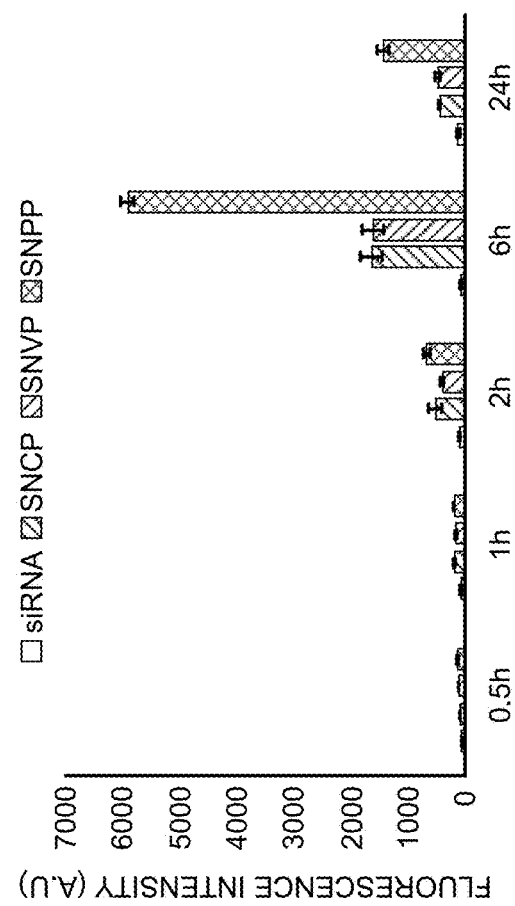
Figure 18:
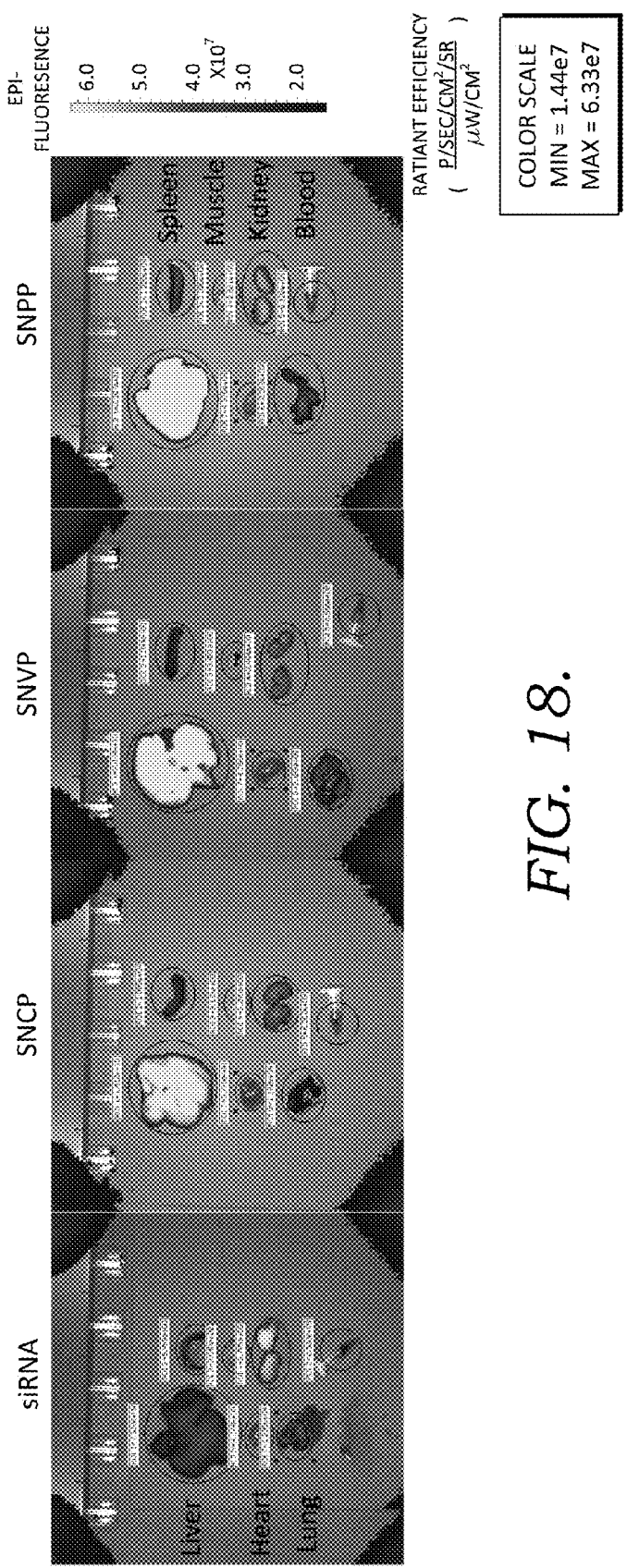
FIG. 18 depicts biodistribution of free siRNA and siRNA nanocomplexes modified with cholesterol (SNCP), Vitamin A (SNVP), and Peptide-431 (SNPP) in rats in accordance with an embodiment of the present invention.

Cellular Uptake of Free siRNA and siRNA Nanocomplexes Modified with Cholesterol (SNCP), Vitamin A (SNVP), and IGF2R-Specific Peptide 431 (SNPP) in HSC-T6 Cells and LX-2 Cells The siRNA was labeled with Alexa Flour-647, and the nanocomplexes were prepared using neutravidin as we reported before. Approximately 100,000 cells (HSC-T6, LX-2)/well were seed into 24 well plate and incubator at 37 C for 12 hrs, free siRNA and nanocomplexes (SNCP, SNVP, SNPP) were then incubated with the cells at a final siRNA concentration of 50 nM. The fluorescence intensity of the cells at different intervals was detected by FACSCalibur Flow Cytometry (BD Biosciences, Franklin Lakes, N.J.). FIG. 17A depicts an evaluation of the cellular uptake of free siRNA and the nanocomplexes in HSC-T6 cells, and FIG. 17B depicts an evaluation of the cellular uptake of free siRNA and the nanocomplexes in LX-2 cells.

Biodistribution of Free siRNA and siRNA Nanocomplexes Modified with Cholesterol (SNCP), Vitamin A (SNVP), and IGF2R-Specific Peptide 431 (SNPP) in Rats The siRNA was labeled with Alexa Flour-647, and the nanocomplexes were prepared using neutravidin as we reported before. The free siRNA and nanocomplexes (SNCP, SNVP, SNPP) were injected into rats by tail vein at an siRNA dose of 0.065 mg/kg. After 2 hrs, the rats were sacrificed and the major organs including the liver, heart, lung, spleen, muscle, kidney, and blood were harvested for fluorescence imaging using a Xenogen IVIS imaging system.

Figure 19:
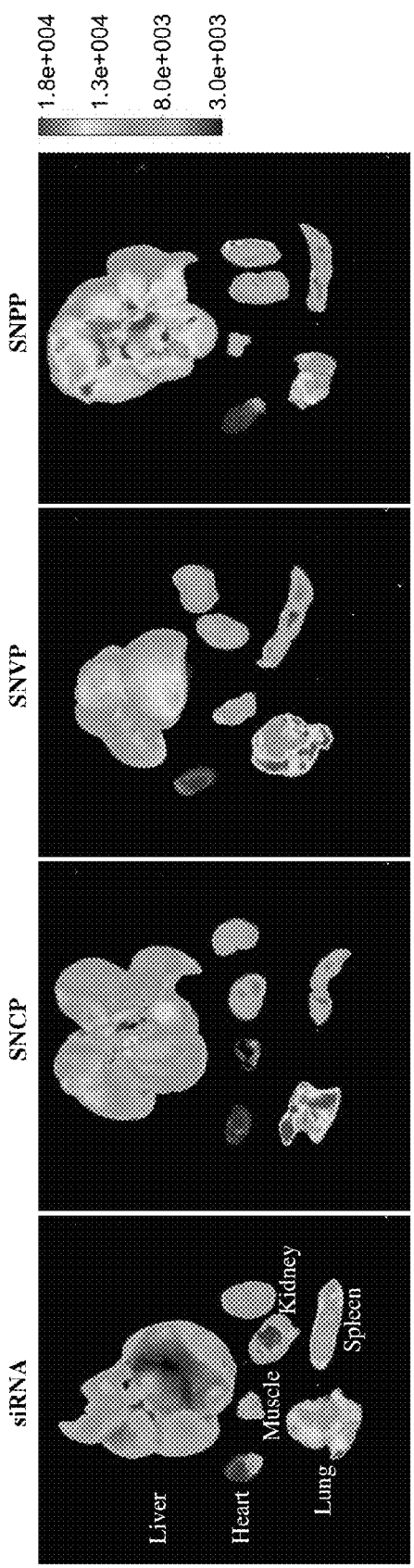
FIG. 19 depicts biodistribution of free siRNA and siRNA nanocomplexes modified with cholesterol (SNCP), Vitamin A (SNVP), and Peptide-431 (SNPP) in rats with liver fibrosis using fluorescence imaging.

Biodistribution of Free siRNA and siRNA Nanocomplexes Modified with Cholesterol (SNCP), Vitamin A (SNVP), and IGF2R-Specific Peptide 431 (SNPP) in Rats with Liver Fibrosis The siRNA was labeled with Alexa Flour-647, and the nanocomplexes were prepared using neutravidin as we reported before. Liver fibrosis was induced by injection of $CCl_4$. The free siRNA and nanocomplexes (SNCP, SNVP, SNPP) were injected into rats with liver fibrosis by tail vein at an siRNA dose of 0.065 mg/kg. After 2 hrs, the rats were sacrificed and the major organs including the liver, heart, lung, spleen, muscle, kidney, and blood were harvested for fluorescence imaging using a small animal imaging system (Brunker MS FX Pro). FIG. 19 depicts images evaluating the biodistribution of free siRNA and the nanocomplexes in Rats with liver fibrosis.

What is claimed is:

1. A composition comprising:
   a polypeptide comprising an amino acid sequence having the amino acid sequence of SEQ ID NO: 6, wherein the polypeptide binds to at least a portion of an insulin-like growth factor 2 receptor (IGF2R) extracellular domain; and
   at least one of an anti-fibrotic agent, an anti-cancer agent, or a proapoptotic agent.

2. The composition according to claim 1, wherein the polypeptide comprises a dimer, wherein the dimer comprises a first and a second amino acid sequence, wherein each of the first and second amino acid sequences has the amino acid sequence of SEQ ID NO: 6.

3. The composition according to claim 2, wherein the first and second amino acid sequences are linked to one another via a linking moiety.

4. The composition according to claim 3, wherein the linking moiety comprises lysine.

5. The composition according to claim 1, wherein the at least one of an anti-fibrotic agent, an anti-cancer agent, or a proapoptotic agent is covalently attached to the polypeptide.

6. A Hepatic stellate cell (HSC) targeting system comprising:
   a targeting composition that comprises:
   a dimeric polypeptide, wherein the dimeric polypeptide comprises a first and a second amino acid sequence, wherein each of the first and second amino acid sequences comprises the amino acid sequence of SEQ ID NO: 6, and wherein the first and second amino acid sequences are linked to one another via a linking moiety; and
   at least one of an anti-fibrotic agent, an anti-cancer agent, or a proapoptotic agent, wherein at least a portion of the dimeric polypeptide binds to at least a portion of an insulin-like growth factor 2 receptor (IGF2R) extracellular domain associated with Hepatic Stellate Cells (HSCs).

7. The HSC targeting system according to claim 6, wherein the targeting composition comprises an anti-fibrotic agent, and wherein the anti-fibrotic agent is covalently attached to at least a portion of the dimeric polypeptide via an attachment moiety.

8. The HSC targeting system according to claim 6, wherein the linking moiety comprises a lysine residue.

9. A composition comprising:
   a polypeptide comprising the amino acid sequence of SEQ ID NO:6; and
   an anti-fibrotic agent covalently attached to at least a portion of the polypeptide.

10. The composition of claim 9, wherein the anti-fibrotic agent comprises the amino acid sequence of SEQ ID NO: 13.

11. The composition of claim 9, wherein the polypeptide comprises a dimer, wherein the dimer comprises a first and a second amino acid sequence, wherein each of the first and second amino acid sequences comprise the amino acid sequence of SEQ ID NO: 6.

12. The composition of claim 9, wherein the polypeptide comprises the amino acid sequence of SEQ ID NO: 6, and wherein the polypeptide exhibits an apparent dissociation constant of about 6.19 µM for LX-2 human hepatic stellate cells.

13. The composition of claim 9, wherein the polypeptide comprises the amino acid sequence of SEQ ID NO: 6, and wherein the polypeptide exhibits an apparent dissociation constant of about 12.35 µM for HSC-T6 rat hepatic stellate cells.

* * * * *